US006661226B1

(12) United States Patent
Hou et al.

(10) Patent No.: US 6,661,226 B1
(45) Date of Patent: Dec. 9, 2003

(54) NMR APPARATUS AND METHODS FOR MEASURING VOLUMES OF HYDROCARBON GAS AND OIL

(75) Inventors: Lei Bob Hou, Houston, TX (US); Daniel Lee Miller, Kingwood, TX (US); James Elmer Galford, Missouri City, TX (US); John C. Bouton, Jr., Doylestown, PA (US); George Richard Coates, Bellville, TX (US); Prabhakar Aadireddy, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 88 days.

(21) Appl. No.: 09/636,502

(22) Filed: Aug. 10, 2000

Related U.S. Application Data

(60) Provisional application No. 60/148,943, filed on Aug. 13, 1999.

(51) Int. Cl.[7] ................................................. G01V 3/00
(52) U.S. Cl. ....................................................... 324/303
(58) Field of Search ......................................... 324/303

(56) References Cited

U.S. PATENT DOCUMENTS

| | | |
|---|---|---|
| 1,158,959 A | 11/1915 | Beach |
| 2,912,641 A | 11/1959 | Ruble |
| 2,973,471 A | 2/1961 | Armistead et al. |
| 3,205,477 A | 9/1965 | Kalbfell |
| 3,213,357 A | 10/1965 | Brown et al. |
| 3,360,716 A | 12/1967 | Bloom et al. |
| 3,395,337 A | 7/1968 | Varian |
| 3,402,344 A | 9/1968 | Brown et al. |
| 3,453,433 A | 7/1969 | Alger et al. ............... 250/83.3 |
| 3,508,438 A | 4/1970 | Alger et al. .................. 73/152 |
| 3,567,935 A | 3/1971 | Nagel ........................ 250/83.1 |
| 3,567,936 A | 3/1971 | Tittman ..................... 250/83.1 |
| 3,590,228 A | 6/1971 | Burke ..................... 235/151.35 |
| 3,593,116 A | 7/1971 | Culpepper ................... 324/0.5 |
| 3,617,867 A | 11/1971 | Herzog ....................... 324/0.5 |
| 3,638,484 A | 2/1972 | Tixier ........................... 73/152 |
| 3,657,730 A | 4/1972 | Robinson et al. ............ 324/0.5 |
| 3,667,035 A | 5/1972 | Slichter .................... 324/0.5 R |
| 3,777,560 A | 12/1973 | Guignard ................... 73/151.5 |

(List continued on next page.)

FOREIGN PATENT DOCUMENTS

| | | | |
|---|---|---|---|
| EP | 0 295 134 A2 | 12/1988 | ............ G01V/3/32 |
| EP | 0 581 666 A3 | 2/1994 | ............ G01V/3/32 |
| EP | 0 649 035 B1 | 4/1995 | ............ G01V/3/32 |
| GB | 2 056 082 A | 7/1980 | .......... G01N/24/08 |
| WO | WO 92/10768 | 6/1992 | ............ G01V/3/32 |
| WO | WO 98/25164 | 6/1998 | ............ G01V/3/32 |

OTHER PUBLICATIONS

Akkurt et al., "Selection of Optimal Acquisition Parameters for MRIL Logs," SPWLA 37th Annual Logging Symposium, Jun. 16–19, 1996.

(List continued on next page.)

*Primary Examiner*—Diego Gutierrez
*Assistant Examiner*—Dixomara Vargas
(74) *Attorney, Agent, or Firm*—Pennie & Edmonds LLP

(57) ABSTRACT

Borehole NMR logging apparatus and methods. A multifrequency method using triple-wait-time is disclosed for determining gas- and light-oil-filled porosity over a broad range of reservoir conditions. The method improves the signal-to-noise ratio and the determination of $T_1$ values for the hydrocarbons, especially when the reservoir contains different fluid types. A set of conditions is derived for the selection of optimum acquisition parameters for logging applications. The data acquisition and processing method enables accurate determination of the pore volumes occupied by each hydrocarbon phase as well as the pore volume occupied by water, as well as accurate $T_1$. A set of conditions is developed to aid in the selection of wait-time combinations appropriate for logging conditions.

17 Claims, 12 Drawing Sheets

U.S. PATENT DOCUMENTS

| | | | | |
|---|---|---|---|---|
| 3,784,898 | A | 1/1974 | Darley et al. | 324/0.5 R |
| 3,896,668 | A | 7/1975 | Anderson et al. | 73/152 |
| 4,291,271 | A | 9/1981 | Lauffer | 324/307 |
| 4,310,887 | A | 1/1982 | Suau | 364/422 |
| 4,350,955 | A | 9/1982 | Jackson et al. | 324/303 |
| 4,479,564 | A | 10/1984 | Tanguy | 181/105 |
| 4,528,508 | A | 7/1985 | Vail, III | 324/303 |
| 4,536,714 | A | 8/1985 | Clark | 324/338 |
| 4,629,986 | A | 12/1986 | Clow et al. | 324/303 |
| 4,656,422 | A | 4/1987 | Vail, III et al. | 324/303 |
| 4,686,364 | A | 8/1987 | Herron | 250/256 |
| 4,707,658 | A | 11/1987 | Frahm et al. | 324/309 |
| 4,710,713 | A | 12/1987 | Strikman | 324/303 |
| 4,714,881 | A | 12/1987 | Givens | 324/303 |
| 4,717,876 | A | 1/1988 | Masi et al. | 324/303 |
| 4,717,877 | A | 1/1988 | Taicher et al. | 324/303 |
| 4,717,878 | A | 1/1988 | Taicher et al. | 324/303 |
| 4,728,892 | A | 3/1988 | Vinegar et al. | 324/309 |
| 4,785,245 | A | 11/1988 | Lew et al. | 324/308 |
| 4,792,757 | A | 12/1988 | Vail, III et al. | 324/303 |
| RE32,913 | E | 4/1989 | Clark | 324/338 |
| 4,825,163 | A | 4/1989 | Yabusaki et al. | 324/318 |
| 4,829,252 | A | 5/1989 | Kaufman | 324/309 |
| 4,875,013 | A | 10/1989 | Murakami et al. | 324/318 |
| 4,885,540 | A | 12/1989 | Snoddy et al. | 324/318 |
| 4,899,112 | A | 2/1990 | Clark et al. | 324/338 |
| 4,933,638 | A | 6/1990 | Kenyon et al. | 324/303 |
| 4,933,640 | A | 6/1990 | Kuckes | 324/339 |
| 4,949,045 | A | 8/1990 | Clark et al. | 324/338 |
| 4,987,368 | A | 1/1991 | Vinegar | 324/303 |
| 4,994,777 | A | 2/1991 | Leupold et al. | 335/302 |
| 5,023,551 | A * | 6/1991 | Kleinberg et al. | 324/303 |
| 5,055,787 | A | 10/1991 | Kleinberg et al. | 324/303 |
| 5,055,788 | A | 10/1991 | Kleinberg et al. | 324/303 |
| 5,122,746 | A | 6/1992 | King et al. | 324/307 |
| 5,138,263 | A | 8/1992 | Towle | 324/338 |
| 5,200,699 | A | 4/1993 | Baldwin et al. | 324/303 |
| 5,212,447 | A | 5/1993 | Paltiel | 324/300 |
| 5,235,285 | A | 8/1993 | Clark et al. | 324/342 |
| 5,280,243 | A | 1/1994 | Miller | 324/303 |
| 5,291,137 | A | 3/1994 | Freedman | 324/303 |
| 5,309,098 | A | 5/1994 | Coates et al. | 324/303 |
| 5,349,184 | A | 9/1994 | Wraight | 250/266 |
| 5,350,925 | A | 9/1994 | Watson | 250/269.3 |
| 5,359,324 | A | 10/1994 | Clark et al. | 340/854.3 |
| 5,363,041 | A | 11/1994 | Sezginer | 324/303 |
| 5,376,884 | A | 12/1994 | Sezginer | 324/303 |
| 5,379,216 | A | 1/1995 | Head | 364/422 |
| 5,381,092 | A | 1/1995 | Freedman | 324/303 |
| 5,387,865 | A | 2/1995 | Jerosch-Herold et al. | 324/303 |
| 5,397,989 | A | 3/1995 | Spraul et al. | 324/321 |
| 5,412,320 | A | 5/1995 | Coates | 324/303 |
| 5,432,446 | A | 7/1995 | MacInnis et al. | 324/303 |
| 5,453,692 | A | 9/1995 | Takahashi et al. | 324/318 |
| 5,486,761 | A | 1/1996 | Sezginer | 324/303 |
| 5,486,762 | A | 1/1996 | Freedman et al. | 324/303 |
| 5,497,087 | A * | 3/1996 | Vinegar et al. | 324/300 |
| 5,498,960 | A | 3/1996 | Vinegar et al. | 324/303 |
| 5,517,115 | A | 5/1996 | Prammer | 324/303 |
| 5,557,200 | A | 9/1996 | Coates | 324/303 |
| 5,557,201 | A | 9/1996 | Kleinberg et al. | 324/303 |
| 5,565,775 | A | 10/1996 | Stallmach et al. | 324/303 |
| 5,629,623 | A | 5/1997 | Sezginer et al. | 324/303 |
| 5,680,043 | A | 10/1997 | Hurlimann et al. | 324/303 |
| 5,696,448 | A * | 12/1997 | Coates et al. | 324/303 |
| 5,705,927 | A * | 1/1998 | Sezginer et al. | 324/303 |
| 5,757,186 | A | 5/1998 | Taicher et al. | 324/303 |
| 5,767,674 | A | 6/1998 | Griffin et al. | 324/303 |
| 5,796,252 | A | 8/1998 | Kleinberg et al. | 324/303 |
| 5,869,755 | A | 2/1999 | Ramamoorthy et al. | 73/152.05 |
| 5,914,598 | A | 6/1999 | Sezginer et al. | 324/303 |
| 5,923,167 | A | 7/1999 | Chang et al. | 324/303 |
| 5,936,405 | A * | 8/1999 | Prammer et al. | 324/303 |
| 5,977,768 | A | 11/1999 | Sezginer et al. | 324/303 |
| 5,992,519 | A | 11/1999 | Ramakrishnan et al. | 166/250.15 |
| 6,005,389 | A | 12/1999 | Prammer | 324/303 |
| 6,008,646 | A | 12/1999 | Griffin et al. | 324/303 |
| 6,023,163 | A * | 2/2000 | Flaum et al. | 324/300 |
| 6,049,205 | A * | 4/2000 | Taicher et al. | 324/303 |
| 6,094,048 | A * | 7/2000 | Vinegar et al. | 324/303 |
| 6,229,308 | B1 * | 5/2001 | Freedman | 324/300 |
| 6,242,912 | B1 * | 6/2001 | Prammer et al. | 324/303 |
| 6,344,744 | B2 * | 2/2002 | Taicher et al. | 324/300 |
| 6,392,409 | B1 * | 5/2002 | Chen | 324/303 |

OTHER PUBLICATIONS

Akkurt et al., "NMR Logging of Natural Gas Reservoirs," SPWLA 36th Annual Logging Symposium (Jun. 26–29, 1995).

Brown et al., "Nuclear Magnetism Logging," Transactions of the American Institute of Mining, Metallurgical, and Petroelum Engineers, vol. 219 (1960), pp. 199–207.

Brownstein et al., "Importance of classical diffusion in NMR studies of water in biological cells," The American Physical Society, vol. 19, No. 6, (1979) pp. 2446–2453.

Cannon et al., "Quantitative NMR Interpretation," Society of Petroleum Engineers, SPE 49010, 1998.

Carr et al., "Effects of Diffusion on Free Precision in Nuclear Magnetic Resonance Experiments," *Physical Review*, vol. 94, No. 3 (May 1, 1954), pp. 630–638.

Chandler et al., "Improved Log Quality with a Dual–Frequency Pulsed NMR Tool," *Society of Petroleum Engineers* (1994) pp. 23–35.

Chandler et al., "Reliable Nuclear Magnetism Logging—With Examples in Effective Porosity and Residual Oil Saturation," SPWLA—28th Annual Logging Symposium, vol. 1, Manuscript C, (1987).

Chen et al., "Improving the Accuracy of NMR Relaxation Distribution Analysis in Clay–Rich Reservoirs and Core Samples," paper SCA 9702, in 1997 international symposium proceedings: Society of Professional Well Log Analysts, Society of Core Analysts Chapter–at–large, p. 10, 1997.

Chen et al., "Estimation of Hydrocarbon Viscosity with Multiple TE Dual Wait–Time MRIL Logs," Society of Petroleum Engineers, SPE 49009, 1998.

Clavier et al., "Theoretical and Experimental Bases for the Dual–Water Model for Interpretation of Shaly Sands," Society of Petroleum Engineers Journal, 1984, pp. 153–168.

Coates et al., "An Investigation of a New Magnetic Resonance Imaging Log," National SPWLA Convention (Jun. 18, 1991),pp. 1–24.

Coates et al., "Applying NMR Total and Effective Porosity to Formation Evaluation," Society of Petroleum Engineers, Inc., SPE 38736, 1997.

Coates et al., "Core Data and the MRIL Show—A New Approach to 'Formation Factor,'" National SPWLA Convention (Jun. 15, 1992), pp. 1–15.

Coates et al., "A New Approach to Improved Log–Derived Permeability," SPWLA Fourteenth Annual Logging Symposium, May 6–9, 1973, pp. 1–27.

Coates et al., "The Magnetic Resonance Imaging Log Characterized by Comparison With Petrophysical Properties and Laboratory Core Data," Society of Petroleum Engineers, SPE 22723, 1991, pp. 627–635.

Dunn et al., "A Method for Inverting NMR Data Sets With Different Signal to Noise Ratios," SPWLA 39th Annual Logging Symposium, May 26–29, 1998.

Edwards et al., "Improved NMR Well Logs From Time–Dependent Echo Filtering," SPWLA 37th Annual Logging Symposium, Jun. 16–19, 1996.

Edwards et al., "Effects of Tool Design and Logging Speed on $T_2$ NMR Log Data," SPWLA 38th Annual Logging Symposium, Jun. 15–18, 1997.

Farrar et al., "Pulse and Fourier Transform NMR Introduction to Theory and Methods," Academic Press (1971) pp. 26–29.

Freedman et al., "Combining NMR and Density Logs for Petrophysical Analysis in Gas–Bearing Formations," SPWLA 39th Annual Logging Symposium, May 26–29, 1998.

Gallegos et al., "A NMR Technique for the Analysis of Pore Structure: Determination of Continuous Pore Size Distributions," Journal of Colloid and Interface Science, vol. 122, No. 1, Mar. 1988, pp. 143–153.

Gallegos et al., "A NMR Technique for the Analysis of Pore Structure: Application to Materials with Well–Defined Pore Structure," Journal of Colloid and Interface Science, vol. 119, No. 1, Sep. 1987, pp. 127–140.

Herrick et al., "An Improved Nuclear Magnetism Logging System and its Application to Formation Evaluation," Society of Petroleum Engineers, SPE 8361, 1979.

Hou et al., "Nuclear Magnetic Resonance Logging Methods for Fluid Typing," Society of Petroleum Engineers, Inc., SPE 48896, 1998.

Howard et al., "Proton Magnetic Resonance and Pore–Size Variations in Reservoir Sandstones," *Society of Petroleum Engineers* (1990), pp. 733–741.

Hull et al., "Field Examples of Nuclear Magnetism Logging," Journal of Petroleum Technology, 1960, pp. 14–22.

Jackson et al., "Western Gas Sands Project Los Alamos NMR Well Logging Tool Development," Los Alamos National Laboratory (Oct. 1981—Sep. 1982) pp. 1–28.

Jasper A. Jackson, "Nuclear Magnetic Resonance Well Logging," The Log Analyst, Sep.–Oct., 1984, pp. 16–30.

Kenyon et al., "Pore–Size Distribution and NMR in Microporous Cherty Sandstones," SPWLA Thirtieth Annual Logging Symposium (Jun. 11–14, 1989), pp. 1–24.

Kleinberg et al., "Novel NMR Apparatus for Investigating an External Sample," *Journal of Magnetic Resonance*, (1992) pp. 466–485.

Kleinberg et al., "Nuclear Magnetic Resonance of Rocks: $T_1$ vs. $T_2$," Society of Petroleum Engineers, SPE 26470, 1993, pp. 553–563.

Kleinberg et al., "NMR Properties of Reservoir Fluids," The Log Analyst, Nov.–Dec. 1996, pp. 20–32.

Menger et al., "A New Algorithm for Analysis of NMR Logging Data," Society of Petroleum Engineers, Inc., SPE 49013, 1998.

Miller et al., "Spin Echo Magnetic Resonance Logging: Porosity and Free Fluid Index Determination," *Society of Petroleum Engineers*, SPE 20561 (1990), pp. 321–334.

Morriss et al., "Field Test of an Experimental Pulsed Nuclear Magnetism Tool," SPWLA Annual Logging Symposium (Jun.13–16, 1993), pp. 1–23.

Morriss et al., "Hydrocarbon Saturation and Viscosity Estimation from NMR Logging in the Belridge Diatomite," 35th SPWLA Annual Logging Symposium (Jun. 19–22, 1994), pp. 1–24.

Nascimento et al., "Anomalous NMR Responses in Highly Permeable Sandstone Reservoirs: A Case Study," SPWLA 40th Annual Logging Symposium, May 30—Jun. 3, 1999.

Neuman et al., "Application of Nuclear Magnetism Logging to Formation Evaluation," Journal of Petroleum Technology, vol. 34, (1982) pp. 2853–2862.

Petrakis et al., "The Utilization of Nuclear Magnetic Resonance Spectroscopy for Petroleum, Coal, Oil Shale, Petrochemicals, and Polymers, Phenomenology, Paradigms of Applications, and Instrumentation," 594 Applied Spectroscopy Reviews vol. 15 (1979) No. 2, pp. 195–260.

Prammer et al., "Theory and Operation Of a New, MultiVolume, NMR Logging System," SPWLA 40th Annual Logging Symposium, May 30–Jun. 3, 1999.

Prammer et al., "A New Multiband Generation of NMR Logging Tools," Society of Petroleum Engineers, SPE 49011, 1998.

Prammer et al., "Measurements of Clay–Bound Water and Total Porosity by Magnetic Resonance Logging," Society of Petroleum Engineers, SPE 36522, 1996.

Prammer, M.G., "NMR Pore Size Distributions and Permeability at the Well Site," *Society of Petroleum Engineers*, SPE 28368, (1994) pp. 55–64.

*Schlumberger Technology News—Oilfield Bulletin*, "Fifth Generation Nuclear Magnetic Resonance Logging Tool: A Major Advance in Producibility Measurement Technology," (Jul. 1995) (2 pp.).

*Schlumberger Wireline & Testing*, "Combinable Magnetic Resonance tool reliably indicates water–free production and reveals hard–to–find pay zones," (Jun. 1995).

Setser et al., "Measurement of Remaining Oil Saturation in Northern Michigan Using Nuclear Magnetism Log Data and Pressure Core," Society of Petroleum Engineers, SPE 14276, 1985.

Singer et al., "Fast NMR Logging for Bound Fluid and Permeability," SPWLA 38th Annual Logging Symposium, Jun. 15–18, 1997.

Straley et al., "NMR in Partially Saturated Rocks: Laboratory Insights on Free Fluid Index and Comparison with Borehole Logs," SPWLA Annual Logging Symposium (Jun. 27, 1991) pp. 40–56.

Tang et al, "LP–ZOOM, a Linear Prediction Method for Local Spectral Analysis of NMR Signals," Journal of Magnetic Resonance 79, 190–196 (1988).

Waxman et al., "Electrical Conductivities in Oil–Bearing Shaly Sands," *Society of Petroleum Engineers Journal* (1968) pp. 107–122.

* cited by examiner

NMR APPARATUS AND METHODS FOR MEASURING VOLUMES OF HYDROCARBON GAS AND OIL

This application claims benefit of provisional application No. 60/148,943 filed Aug. 13, 1999.

FIELD OF THE INVENTION

The present invention relates to borehole measurements and more particularly to a system and method for detecting the presence and estimating the quantity of gaseous and liquid hydrocarbons using nuclear magnetic resonance.

BACKGROUND

Various methods exist for performing measurements of petrophysical parameters in a geologic formation. Nuclear magnetic resonance (NMR) logging, which is the focus of this invention, is among the best methods that have been developed for a rapid determination of such parameters, which include formation porosity, composition of the formation fluid, the quantity of movable fluid and permeability, among others. NMR measurements are environmentally safe and are essentially unaffected by matrix mineralogy, because NMR signals from the matrix decay too quickly to be detected by the current generation NMR logging tools. Thus, unlike conventional neutron, density, sonic, and resistivity logs, NMR logs provide information only on formation fluids. Importantly, however, NMR tools are capable of directly measuring rock porosity filled with the fluids. Even more important is the unique capability of NMR tools, such as NUMAR Corporation's MRIL® tool to distinguish among different fluid types, in particular, clay-bound water, capillary-bound water, movable water, gas, light oil, medium oil, and heavy oil by applying different sets of user-adjusted measurement parameters. (MRIL is a mark of NUMAR Corporation, a Halliburton company). This ability to detect the presence and estimate the volumes of different types of fluids is becoming one of the main concerns in the examination of the petrophysical properties of a geologic formation.

To better appreciate how NMR logging can be used for fluid signal separation and estimating fluid volumes, it is helpful to briefly examine the type of parameters that can be measured using NMR techniques. It is well known that when an assembly of magnetic moments, such as those of hydrogen nuclei, are exposed in a NMR measurement to a static magnetic field they tend to align along the direction of the magnetic field, resulting in bulk magnetization. The rate at which equilibrium is established in such bulk magnetization upon provision of a static magnetic field is characterized by the parameter $T_1$, known as the spin-lattice relaxation time. Another related and frequently used NMR logging parameter is the spin-spin relaxation time $T_2$ (also known as transverse relaxation time), which relaxation is the loss of transverse magnetization due to non-homogeneities varying in time in the local magnetic field over the sensing volume of the logging tool. Both relaxation times provide information about the formation porosity, the composition and quantity of the formation fluid, and others.

Another measurement parameter obtained in NMR logging is the diffusion of fluids in the formation. Generally, diffusion refers to the motion of atoms in a gaseous or liquid state due to their thermal energy. Self-diffusion is inversely related to the viscosity of the fluid, which is a parameter of considerable importance in borehole surveys. In a uniform magnetic field, diffusion has little effect on the decay rate of the measured NMR echoes. In a gradient magnetic field, however, diffusion causes atoms to move from their original positions to new ones, which moves also cause these atoms to acquire different phase shifts compared to atoms that did not move. This effect contributes to a faster rate of relaxation in a gradient magnetic field.

NMR measurements of these and other parameters of the geologic formation can be done using, for example, the centralized MRIL® tool made by NUMAR Corporation, a Halliburton company, and the sidewall CMR tool made by Schlumberger. The MRIL® tool is described, for example, in U.S. Pat. No. 4,710,713 to Taicher et al. and in various other publications including: "Spin Echo Magnetic Resonance Logging: Porosity and Free Fluid Index Determination," by Miller, Paltiel, Gillen, Granot and Bouton, SPE 20561, 65th Annual Technical Conference of the SPE, New Orleans, La., Sep. 23–26, 1990; "Improved Log Quality With a Dual-Frequency Pulsed NMR Tool," by Chandler, Drack, Miller and Prammer, SPE 28365, 69th Annual Technical Conference of the SPE, New Orleans, La., Sep. 25–28, 1994. Certain details of the structure and the use of the MRIL® tool, as well as the interpretation of various measurement parameters are also discussed in U.S. Pat. Nos. 4,717,876; 4,717,877; 4,717,878; 5,212,447; 5,280,243; 5,309,098; 5,412,320; 5,517,115, 5,557,200; 5,696,448 and 5,936,405, all of which are commonly owned by the assignee of the present invention. The Schlumberger CMR tool is described, for example, in U.S. Pat. Nos. 5,055,787 and 5,055,788 to Kleinberg et al. and further in "Novel NMR Apparatus for Investigating an External Sample," by Kleinberg, Sezginer and Griffin, J. Magn. Reson. 97, 466–485, 1992. The content of the above patents and publications is hereby expressly incorporated by reference.

It has been observed that the mechanisms determining the measured values of $T_1$, $T_2$ and diffusion depend on the molecular dynamics of the formation fluids being tested and on the types of fluids present. Thus, in bulk volume liquids, which typically are found in large pores of the formation, molecular dynamics is a function of both molecular size and inter-molecular interactions, which are different for each fluid. Water, gas and different types of oil each have different $T_1$, $T_2$ and diffusivity values. On the other hand, molecular dynamics in a heterogeneous media, such as a porous solid that contains liquid in its pores, differs significantly from the dynamics of the bulk liquid, and generally depends on the mechanism of interaction between the liquid and the pores of the solid media. It will thus be appreciated that a correct interpretation of the measured signals can provide valuable information relating to the types of fluids involved, the structure of the formation and other well-logging parameters of interest.

If the only fluid in the formation is brine, a Carr-Purcell-Meiboom-Gill (CPMG) pulse sequence with a short inter-echo spacing ($T_e$) and a long wait-time ($T_w$) can be applied for porosity determination and identification of capillary-bound and free water volumes. Total porosity logging methods are available to improve the quality of data used for determining pore volumes occupied by clay-bound and/or capillary-bound water. (See, for example, Prammer, M. G., et al.: "Measurements of Clay-Bound Water and Total Porosity by Magnetic Resonance Logging," paper SPE 36522 presented at the 1996 SPE Annual Technical Conference and Exhibition, Denver, October 6–9). However, if hydrocarbons, such as formation oil and/or gas or filtrate from oil-based mud, coexist with brine, porosity determination and fluid typing (identification and quantification) with NMR becomes more difficult.

Additional difficulties arise from the fact that NMR measurements impose limitations on the logging speed. For example, it is known in the art that for porosity determination all stimulated fluid protons should be sampled at full polarization. Therefore, a long wait time $T_w$ is required to completely detect the magnetization from protons in slow $T_1$ processes. For gas and light oil under typical formation conditions of temperature and pressure (100–300° F. and 2,000–10,000 psi), $T_1$ values of a few seconds occur at low-frequency (1- to 2-MHz) NMR. Wait times $T_w$ of at least 10 seconds will capture nearly all the total proton magnetization arising from the individual $T_1$ recovery rates encountered in petroleum logging. Such long wait times, combined with acceptable depth sampling, restrict the logging speed and reduce wellsite efficiency. One approach addressing this problem is the application of prepolarization and multislice (multifrequency) acquisitions implemented in the Magnetic Resonance Imaging Logging™ MRIL-Prime tool. See Prammer, M. G., et al.: "Theory and Operation of a New Multi-Volume NMR Logging System," paper DD presented at the $40^{th}$ Annual SPWLA Logging Symposium, Oslo, Norway, May 30–Jun. 3, 1999. Still, it is believed that the capabilities of the MRIL tool have not yet been fully utilized.

Turning to the problem of fluid typing by NMR, it is known that it relies on contrasts of characteristic parameters of the fluids, such as $T_1$, $T_2$, and diffusivity. Two or more CPMG data sets, which may not be completely polarized, are usually acquired to exploit parameter contrasts among the expected fluids. Using NMR logging to determine reservoir porosity occupied by gas or light oil currently requires data simultaneously acquired from at least two CPMG sequences having different wait-times. Examples of this method are disclosed in U.S. Pat. No. 5,936,405 to the assignee of the present application. The content of this patent is incorporated herein by reference for all purposes.

Dual-wait-time and dual-frequency methods have been applied to determine gas volumes in both clean and shaley sand formations. It is known that the success of the application depends primarily on two factors. First, adequate signal-to-noise levels in an echo train difference has to be maintained so that the gas-filled porosity and its transverse relaxation time $T_2$ can be accurately characterized. Second, methods must be available to reliably estimate the longitudinal relaxation time $T_1$ of the hydrocarbon phase needed to apply a necessary amplitude correction to the apparent hydrocarbon-filled porosity. It is clear that data acquisition and processing methods that address these two factors with success are highly desirable.

NMR technology has been successfully applied to distinguish fluids, and significant progress has been made in determining porosity in mixed-fluid situations. The reader is directed for details to the disclosure of U.S. provisional patent application Ser. No. 60/106,259, filed Oct. 30, 1998 to the assignee of the present application. The content of this application is incorporated herein by reference for all purposes. Still, quantitative analysis to determine actual hydrocarbon volumes present in the instrument's measurement space remains difficult because polarization corrections applied to apparent hydrocarbon volumes rely on accurate knowledge of the hydrocarbon $T_1$.

Several researchers have acknowledged the importance of $T_1$ in quantitative fluid typing. Obtaining enough saturation-recovery data points to derive an accurate and precise $T_1$ distribution of a fluid at acceptable logging speeds and vertical resolution is difficult or nearly impossible. Consequently, most quantitative analyses rely on $T_1$ values computed from correlation functions or by the application of assumptions to measured values. One disadvantage of such methods is that formation parameters, such as temperature, pressure, and fluid viscosity, may not be accurately known. In addition, attention must be directed to the ranges for which the correlation functions are valid. Prior art methods of deriving $T_1$ involve either dual $T_w$'s with one inter echo spacing $T_e$ or dual $T_w$'s with multiple $T_e$'s. See Akkurt, R., Prammer, M. G., and Moore, M. A.: "Selection of Optimal Acquisition Parameters for MRIL Logs," *The Log Analyst* (November–December 1996) 43; and Chen, S., et al.: "Estimation of Hydrocarbon Viscosity with Multiple TE Dual Wait-Time MRIL Logs," paper SPE 49009 presented at the 1998 SPE Annual Technical Conference and Exhibition, New Orleans, September 27–30. Both methods referenced above assume that oil (or unpolarized brine) $T_2$ signals are totally separated from brine $T_2$ signals, which assumption is sometimes incorrect. Methods for obtaining gas $T_1$ values from NMR logs have not been previously developed.

In addition to being an important parameter for correcting apparent volumes of fluids for under-polarization, $T_1$ computations play an important role in distinguishing one fluid from another. For example, it is well known that gas and light oil have large $T_1$ values, and thus can be separated from brine, which typically has lower values for $T_1$. Furthermore, fluid viscosity and self-diffusion coefficient D that can be obtained from a known $T_1$ value can be used to separate gas from other fluids. Thus, large values for both $T_1$ and D reliably indicate the presence of gas or light oil in a formation. Fluid viscosity can also be used in grouping liquids. Various additional contrast mechanisms are known in the art and are described, for example, in the above-referenced U.S. provisional application No. 60/106,259, filed Oct. 30, 1998 to the assignee of the present application. Because $T_1$ relaxation times are not influenced by interactions between magnetic gradients and molecular diffusion, fluid viscosities obtained from measured $T_1$'s are believed to be superior to other methods whenever a gradient-field logging tool is used or an internal magnetic gradient from the formation is present.

In view of the shortcomings of the prior art briefly outlined above, it is apparent that there is a need for a method and system that can take full advantage of the flexibility provided by current-generation NMR tools to enable the accurate calculation of $T_1$ and $T_2$ parameters for different fluids over the range of geologically meaningful values. This calculation in turn will enable reliable detection of the presence of gaseous and liquid hydrocarbons and estimation of their quantities.

SUMMARY OF THE INVENTION

Accordingly, it is an object of the present invention to provide a method and apparatus using nuclear magnetic resonance (NMR) techniques that obviate problems associated with the prior art.

In particular, a new triple-wait-time, multi-frequency acquisition method is disclosed and successfully tested. The method takes advantage of the multi-frequency operation of modern NMR logging tools to improve the signal-to-noise ratio of the received signals at high logging speeds. Further, the acquisition method enables accurate estimation of volumes for hydrocarbon and/or free water in addition to traditional clay-bound and capillary-bound water volumes.

The new acquisition method uses optimized wait times to obtain better signal-to-noise ratios in echo train differential signals at faster logging speeds and acceptable vertical resolution. In turn, these signals can be used to determine formation fluid volumes, as well as estimates of hydrocarbon $T_1$. Experiments performed on a mixture of dodecane ($C_{12}H_{26}$) and doped water, $C_{12}H_{26}$ and brine in a sandstone core, and fresh water produced fluid volumes with absolute errors of less than 1.5% for echo train differences with a signal-to-noise ratio larger than 4:1.

In another aspect, the present invention provides a data processing method that enables the accurate determination of both $T_2$ and $T_1$ parameters of hydrocarbons based on the use of at least two difference NMR signals obtained at different wait times. The data acquisition and processing method of the present invention enable the determination of gas- and light-oil-filled porosity over a broad range of reservoir conditions. In another aspect, the present invention provides a decision mechanism to help in the selection of optimum acquisition parameters for logging applications.

In particular, in accordance with the present invention is provided a (NMR) data acquisition method, comprising: providing a first set of CPMG pulses associated with a first relatively short recovery time $T_{WS1}$; providing a second set of CPMG pulses associated with a second relatively short recovery time $T_{WS2}$, where $T_{WS2}$ is longer than $T_{WS1}$; providing a third set of CPMG pulses associated with a relatively long recovery time $T_{WL1}$; receiving NMR echo signals from a population of particles in response to the first, second and third sets of CPMG pulses; and processing the received NMR echo signals to provide a data representation associated with the longitudinal relaxation time constant $T_1$ of the population of particles.

In specific embodiments, the steps of providing the first, second and third sets of CPMG pulses are interleaved in time and/or are acquired in different sensitive volumes. In these embodiments, the steps of providing the first, second and third sets of CPMG pulses are performed using a multi-frequency NMR logging tool. In different specific embodiments CPMG pulses associated with different recovery times may have either same or different operating frequencies. In a preferred embodiment, the first and second short recovery times $T_{WS1}$ and $T_{WS2}$ are selected long enough to substantially polarize a water phase component in the population of particles, or in such manner that water-phase contribution is substantially canceled in a difference signal formed by subtracting NMR signals corresponding to a relatively short recovery time from NMR signals corresponding to the relatively long recovery time $T_{WL1}$.

In another aspect, in accordance with the present invention is provided a method for conducting NMR logging measurements, comprising: providing a data acquisition sequence comprising at least two sets of CPMG pulses having relatively short recovery times $T_{WS1}$ and $T_{WS2}$, respectively, and at least one set of CPMG pulses having relatively long recovery time $T_{WL1}$; receiving NMR echo signals from a population of particles in a geologic formation in response to the provided sets of CPMG pulses; processing the received NMR echo signals to determine a first and a second apparent volumes for at least one hydrocarbon fluid phase of the geologic formation, said first apparent volume being determined from a data representation associated with signals having short recovery time $T_{WS1}$, and the second apparent volume being determined from a data representation associated with signals having short recovery time $T_{WS2}$; providing a data representation associated with the longitudinal relaxation time constant $T_1$ of said at least one hydrocarbon fluid phase based on the determined first and second apparent volumes.

In a specific embodiment processing the received NMR echo signals comprises: forming a first difference signal Edif1 by subtracting NMR signals having relatively short recovery time $T_{WS1}$ from NMR echo signals having relatively long recovery time $T_{WL}$; computing $T_2$ distribution of the first difference signal Edif1; and determining a value for the $T_2$ relaxation time of said at least one hydrocarbon phase. In another embodiment, the method further comprises forming a second difference signal Edif2 by subtracting NMR signals having relatively short recovery time $T_{WS2}$ from NMR echo signals having relatively long recovery time $T_{WL}$. In a preferred embodiment, the method further comprises the step of computing the total porosity of the formation $\phi_t$ from the total apparent porosity $\phi_{ta}$ and apparent volume corrections computed based on the provided data representation associated with the longitudinal time constant (s) $T_1$ of the fluid phases.

In another aspect, the present invention is a method of operating a multi-volume NMR logging tool, comprising: (a) acquiring a first NMR echo train or sets of echo trains in a first sensitive volume of the tool, said first echo train(s) carrying information about NMR signals with recovery time $T_{WS1}$; (b) acquiring a second NMR echo train or sets of echo trains in a second sensitive volume of the tool, said second echo train(s) carrying information about NMR signals having recovery time $T_{WL}$; (c) acquiring a third NMR echo train or sets of echo trains, said third echo train(s) carrying information about NMR signals with recovery time $T_{WS2}$; (d) computing values for the transverse relaxation time $T_2$ and apparent volume for at least one hydrocarbon fluid phase based on the acquired NMR echo trains; and (e) providing a data representation associated with the longitudinal relaxation time constant $T_1$ of said at least one hydrocarbon fluid phase based on the determined first and second apparent volumes.

In another aspect, the present invention is a NMR data processing method for use in borehole logging, comprising: selecting values for a second relatively short recovery time $T_{WS2}$ using a known functional relationship based on estimates of: (a) a first relatively short recovery time $T_{WS1}$ needed to polarize water signals in a geologic formation surrounding the borehole; and (b) expected $T_1$ values for hydrocarbon fluid phases in the geologic formation surrounding the borehole; providing a data acquisition sequence comprising at least two sets of CPMG pulses having said relatively short recovery times $T_{WS1}$ and $T_{WS2}$, respectively, and at least one set of CPMG pulses having relatively long recovery time $T_{WL}$; processing NMR echo signals received in response to the data acquisition sequence to provide an estimate of the true values for the longitudinal relaxation time constant $T_1$ of hydrocarbon fluid phases in the geologic formation, wherein the accuracy of the estimates of the $T_1$ constant is controlled in the step of selecting.

BRIEF DESCRIPTION OF THE DRAWINGS

The present invention will be understood and appreciated more fully from the following detailed description taken in conjunction with the drawings in which.

DESCRIPTION OF PREFERRED EMBODIMENTS

A. Equipment

Figure 12:
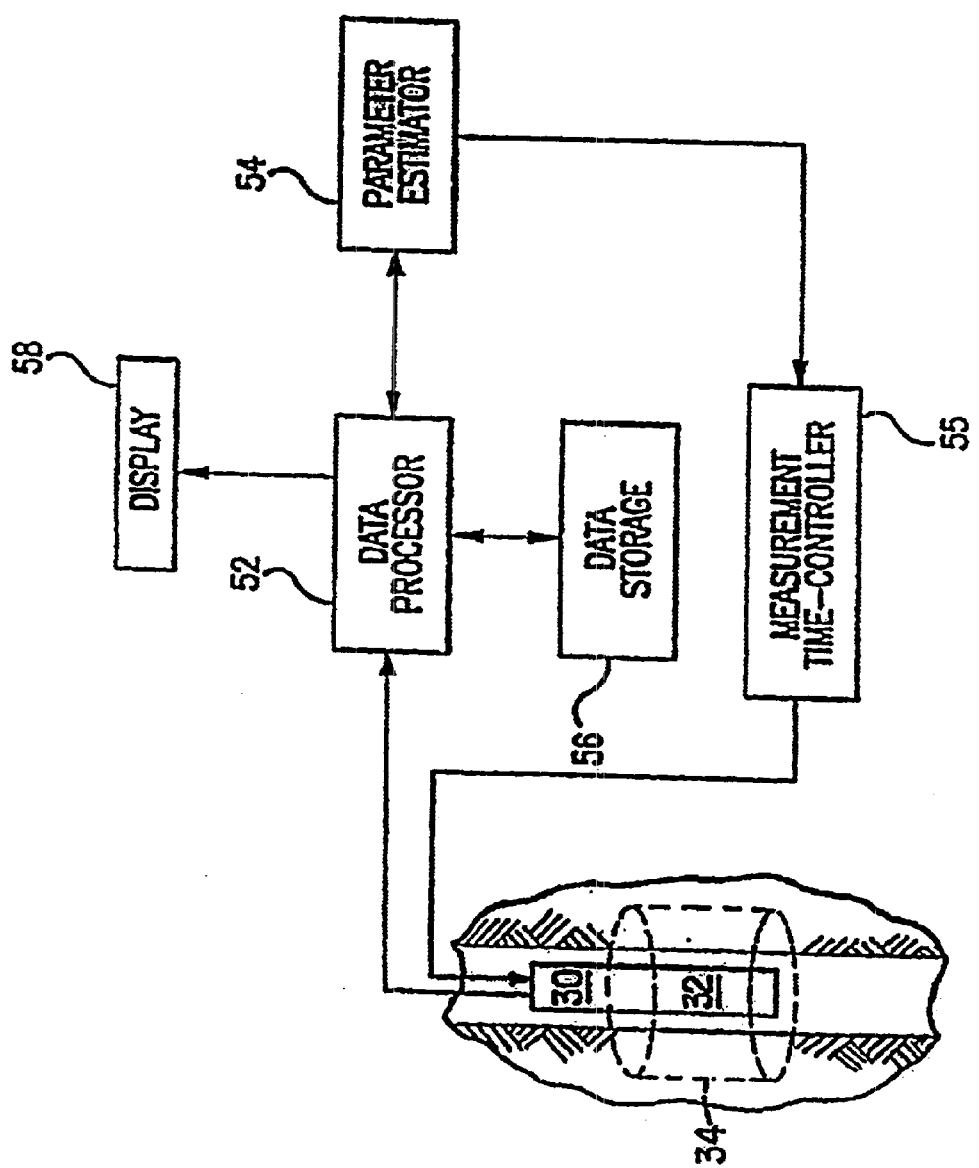
FIG. 12 is a block diagram of the apparatus in accordance with a preferred embodiment, which shows individual block components for controlling data collection, processing the collected data and displaying the measurement results.

In accordance with the present invention, NMR measurements are made using tools capable of performing separate, quasi-simultaneous measurements in different sensitive volumes by switching the operating frequency of the tool. FIG. 12 is a block diagram of a generic system used in accordance with the present invention, and shows individual block components for controlling data collection, for processing the collected data and displaying the measurement results. As shown in FIG. 12, the system has a portion 32 (generally comprising a magnet array and antenna(s)) which is arranged to be lowered into a borehole. The tool's electronic section 30 comprises a probe controller and pulse echo detection electronics. The output signal from the detection electronics is processed by data processor 52 to analyze the relaxation characteristics of the material being investigated in the sensitive volume, generally designated as 34. The output of the data processor 52 is provided to the parameter estimator 54. Generally, data processor 52 selects the desired data acquisition technique and the corresponding set of measurement parameters.

Dependent on the selected data acquisition technique, measurement cycle controller 55 provides an appropriate control signal to the probe. In a specific embodiment, data from the log measurement is stored in data storage 56. In a preferred embodiment, raw data received by the tool can be pre-processed downhole by the electronic section 30. Data processor 52 is connected to display 58, which is capable of providing a graphical display of one or more measurement parameters, possibly superimposed on display data from data storage 56.

For the purposes of this invention it is important that the tool is capable of "hopping" from one operating frequency to another, the effect of which is to shift the radial position of the resonant volume of the tool. The frequency shift is selected in such manner that two or more non-overlapping resonant volumes are formed; each new resonant volume associated with a different frequency being filled with fully relaxed protons. Hopping between two or more (i.e., K) frequencies thus allows reducing the time between experiments approximately by a factor of K, without compromising complete $T_1$ measurements or adopting imprecise empirical $T_1/T_2$ relationships; the logging speed for the tool can accordingly be increased approximately K times.

The components of the system of the present invention shown in FIG. 12 can be implemented in hardware or software, or any combination thereof suitable for practical purposes. Preferably, the data processing algorithms used in accordance with the invention are programmed into software which is stored in a computer storage medium for execution on a computer, such as data processor 52. In a preferred embodiment, NMR measurements in accordance with the present invention are done using Numar Corporation's (a Halliburton Company) MRIL® tools having multi-frequency capability, such as the MRIL®-Prime tool. Details of the structure, the operation and the use of logging tools, as illustrated in FIG. 12, are also discussed, for example, in U.S. Pat. Nos. 4,717,876; 4,717,877; 4,717,878; 5,212,447; 5,280,243; 5,309,098; 5,412,320; 5,517,115; 5,557,200; 5,696,448 and 5,936,405 to the assignee of the present application, the contents of which are incorporated herein for all purposes.

B. Data Acquisition

In accordance with a preferred embodiment of the present invention, the multi-frequency capability of the operating tool is used to provide a new data acquisition method, which is particularly suitable for the detection of gas and other hydrocarbons on the basis of NMR measurements with different wait times $T_W$. To this end, with reference to FIG. 1, a novel interleaved pulse sequence is proposed using triple-wait-time activation.

Figure 1:
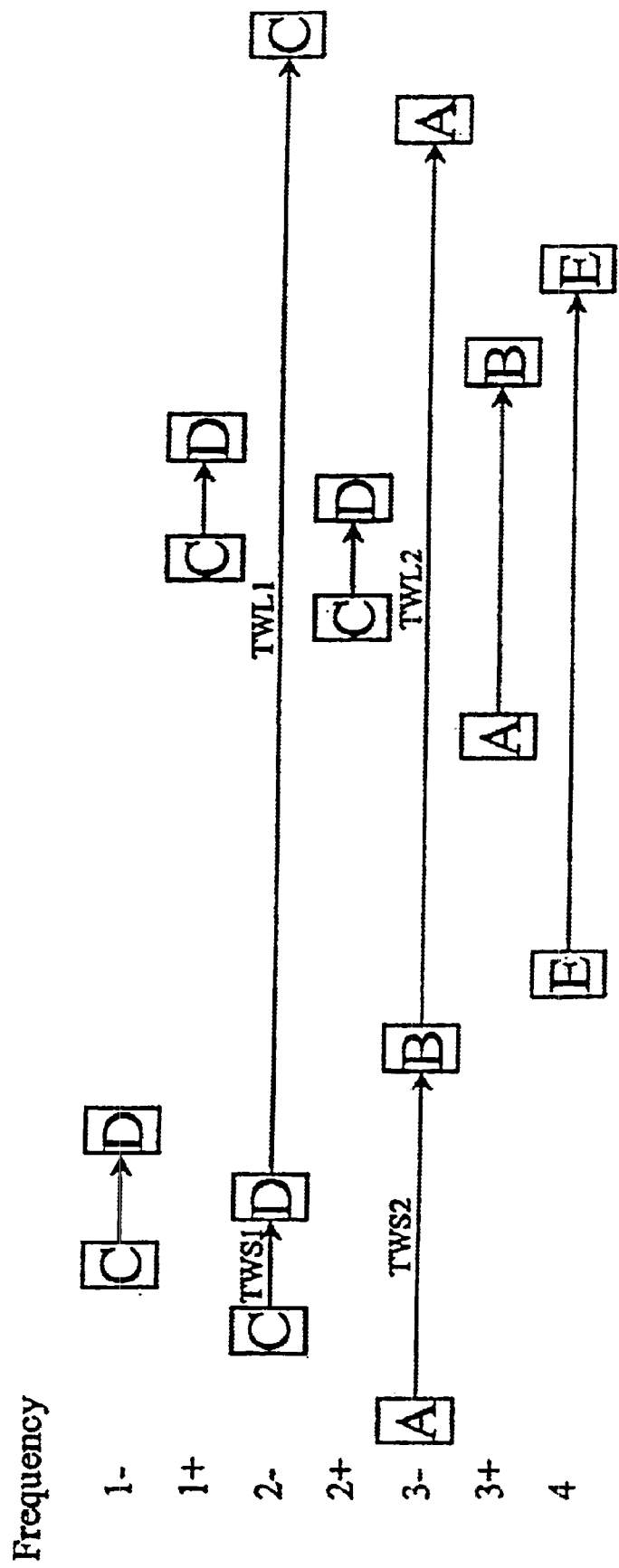
FIG. 1 is an illustration of the triple-wait time activation sequence used in a preferred embodiment of the present invention.

FIG. 1 generally illustrates a method for measuring volumes occupied by hydrocarbons, and in particular shows a triple-wait-time activation sequence of the preferred embodiment. As shown, the activation sequence used in a preferred embodiment of the present invention uses seven resonant frequencies, which are grouped into four frequency bands designated 1, 2, 3, and 4. The specific frequencies used in these four bands depend on the characteristics of the tool and the desirable sensitive volume. In a specific embodiment using Numar Corporation's MRIL tool, the nominal center frequencies for bands 1, 2, 3 and 4 shown in FIG. I are 620 kHz, 650 kHz, 680 KHz and 760 kHz, respectively. As shown, in a preferred embodiment of the method there are two frequencies each corresponding to frequency bands 1, 2, and 3. These two frequencies, denoted in FIG. 1 by plus and minus signs appended to the band number, are +6 and −6 kHz relative to the band center frequency in a specific embodiment. In the embodiment illustrated in FIG. 1, band 4 is a single frequency band that operates at a nominal frequency of 760 kHz for the MRIL tool. It can be shown that in this embodiment the radial distance between the inner- and outer-most sensitive volumes is less than one inch.

For ease of notation, data groups acquired using identical wait times $T_W$ have identical labels, and are designated A, B, C, D and E. As shown in FIG. 1, in general there are four wait times involved in the measurements performed at the 1−, 1+, 2−, 2+, 3−, and 3+ frequencies—two relatively short wait times designated $T_{WS1}$ and $T_{WS2}$, and two relatively long wait times, $T_{WL1}$ and $T_{WL2}$. However, at normal logging speeds measurement volumes with these frequencies are completely replenished with protons that have been fully polarized during the $T_{WL1}$ and $T_{WS2}$ delays. For example, this may be due to the length of the wait time interval and/or the use of pre-polarizing magnets. Thus, for practical purposes the activation sequence of the present invention effectively involves only one long wait time $T_{WL}$, which is used for data processing purposes. In a preferred embodiment this wait time $T_{WL}$ is selected as the longest delay time $T_{WL1}$ shown in FIG. 1.

Figure 2:
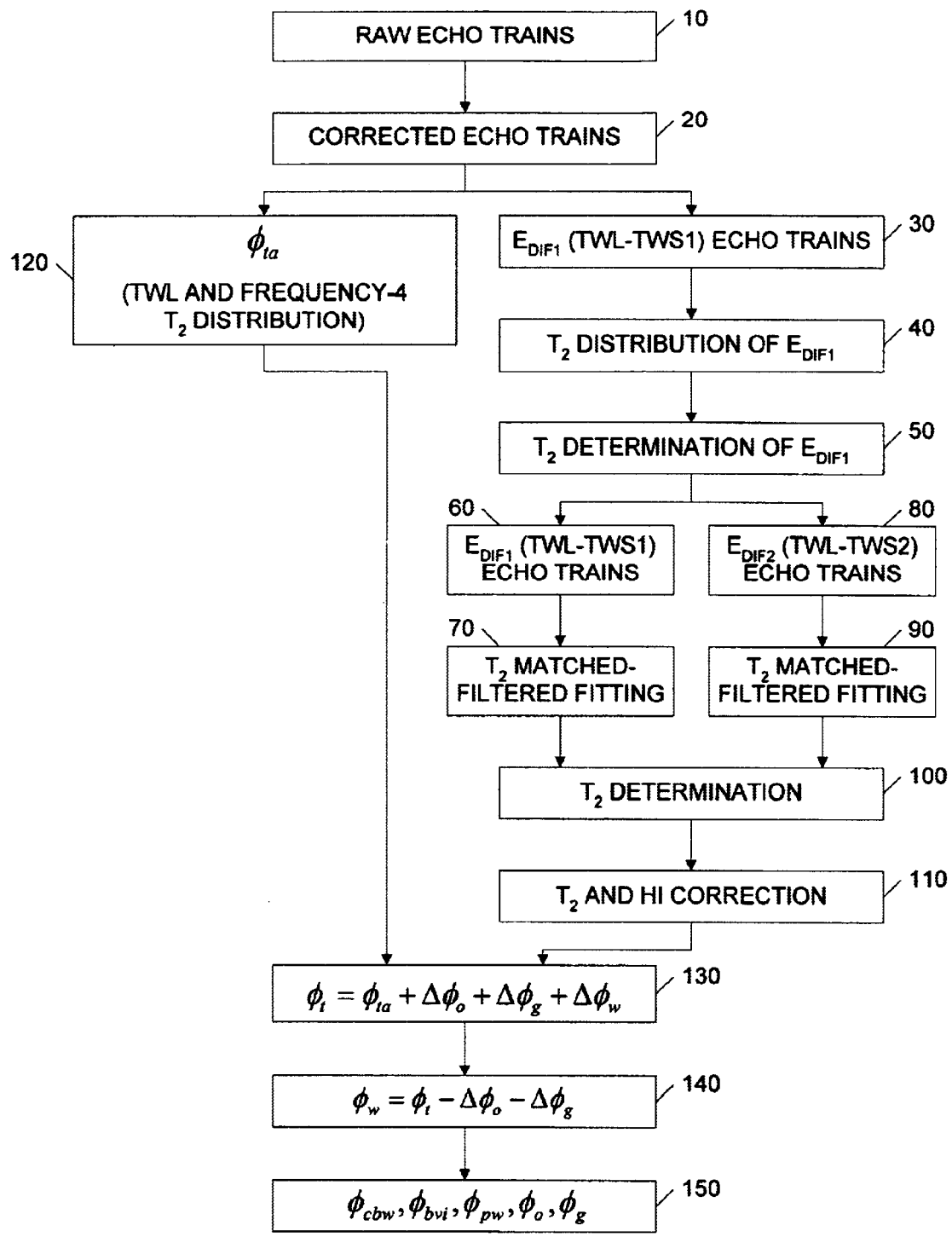
FIG. 2 is a flow diagram illustrating the data processing method used in a preferred embodiment of the present invention.

In accordance with the present invention, and with further reference to FIG. 2, four frequencies (1−, 1+, 2−, and 2+) in the activation sequence shown in FIG. 1 provide improved signal-to-noise ratio in echo train differences compared with prior art data acquisitions made with dual-frequency tools. As explained below, measurements performed at these frequencies (data groups C and D) are generally used to obtain $T_2$ estimates and apparent hydrocarbon volumes. On the other hand, NMR signals obtained from the combination of the 1−, 1+, 2−, 2+, 3−, and 3+ frequencies (data groups A, B, C and D) are used in accordance with the present invention to determine hydrocarbon $T_1$ values. In turn, these values are used to make polarization corrections to apparent hydrocarbon volumes derived from the 1−, 1+, 2−, and 2+ frequency measurements.

In a preferred embodiment, measurements at frequency band 4 (data groups E in FIG. 1) consist of a small number of high-quality echoes. Data groups E are used to improve the precision in measuring rapid $T_2$ decay components usually associated with clay-bound water and/or capillary-bound water.

In accordance with the present invention, the design of the activation sequence illustrated in a preferred embodiment in FIG. 1 also improves the logging speed of the tool. It is known in the art that under the influence of tool motion, RF, magnetic field values, and sensitive volume can not be constant at a particular location in a formation. See, for example, Edwards, C. M.: "Effects of Tool Design and Logging Speed on T2 NMR Log Data," paper RR presented at the 38$^{th}$ Annual SPWLA Logging Symposium, Houston, Jun. 15–18, 1997. As a consequence, apparent $T_2$ values decrease with increasing logging speed. It is clear that the addition of more frequencies (measurement volumes) in accordance with the present invention causes a larger volume of formation to be sampled per unit length of tool motion, so that a greater signal-to-noise ratio (SNR) is attained. In the alternative, for a given SNR one can obtain higher logging speed. It has been determined that for the acquisition sequence illustrated in FIG. 1, using the MRIL tool of the preferred embodiment, the maximum logging speed is about 900 ft/hr, which gives a vertical resolution of approximately 3 ft and minimizes the influence of logging speed on $T_2$ determination.

It will be appreciated by those of skill in the art that in alternative embodiments of this invention a different, for example larger, number of frequency bands and/or frequencies per band can be used in the activation sequence. It should be apparent that in such alternative embodiments one can increase the SNR of the received signals by combining more data groups per data point. For example, with reference to FIG. 1, instead of two data groups C for the first data point (one at frequency band 1− and one at frequency band 2−) one can use a higher number. In an alternative embodiment, a single data group can be used per data point. As illustrated in FIG. 1, data for the three different recovery times need not necessarily be obtained from only three different frequencies. For example, two or more measurements associated with different frequencies can be combined (i.e., averaged) to result in a single data stream corresponding to either a short, or a long recovery time. Additional modifications in the parameters of the pulse sequences can be applied, as known in the art. For example, it is known that the contrast between liquid and gas signals can be enhanced by using a slightly larger pulse-echo spacing for the CPMG train associated with the shorter recovery interval. Modifications of this type are straightforward extensions of the activation sequence illustrated in FIG. 1.

The activation sequence illustrated in a preferred embodiment in FIG. 1 is believed to have at least two significant advantages over the prior art, including dual-$T_W$, dual-frequency methods for determining volumes of gas or light oil. First, the addition of more frequencies (measurement volumes) causes a larger volume of formation to be sampled per unit length of tool motion so that a greater signal-to-noise ratio (SNR) is attained in the echo train differential signals used to determine apparent hydrocarbon volumes. Second, the acquisition sequence has the important advantage that interlaced measurements having three wait times enable the computation of $T_1$ values for the hydrocarbon phases in the formation, as shown below.

C. Data Processing

In accordance with a preferred embodiment of the present invention, data acquired with the new activation sequence discussed above is processed as shown in FIG. 2. In particular, at step 10 raw echoes are received according to a triple-wait-time activation sequence, such as shown in FIG. 1. In step 20, in a preferred embodiment the method applies certain corrections to the raw data generally designed to improve the signal-to-noise ratio of the received signal. In a specific embodiment, in step 20 the raw data undergoes a phase correction and/or a running average correction. Both corrections are known in the art and thus will not be considered in detail. For purposes of illustration, in a specific embodiment implementing phase correction, if r(n) is the magnitude for the nth echo in a CPMG echo train, and a(n) is its angle (in radians) the phase correction for the CPMG echo train is given by the following pseudo-code:
First find the Phase correction angle A over a group of M echos (where M=2–10 in a specific embodiment)

$$R^* \exp(j^*A) = \text{sum}[r(n)^* \exp \cdot (j^*a(n))], n=1, \ldots, M,$$

2) Apply phase correction, i.e., phase rotation to the individual echos using $$r(n)^* \exp \cdot (j^*a(n))^* \exp(-j^*A)$$

3) obtain phase corrected values using $$\text{Echoes} = \text{Re}\{r(n)^* \exp \cdot (j^*a(n))^* \exp(-j^*A)\}$$

where Re{·} is taking the real part.

It will be appreciated that the above processing sequence separates signal with noise in one channel and noise only in the secondary channel (i.e., the imaginary part following the correction), and has the additional benefit of reducing the original complex number representation to working with real numbers.

In a specific embodiment, a running average correction (using 8 or 16 echos) can also be applied as known in the art in step 20 to further improve the signal-to-noise ratio.

With reference to FIG. 2, following step 20 the processing algorithm is separated into two branches. Generally, hydrocarbon volumes and $T_1$ estimates are determined in the right branch. In the left branch, the long $T_W$ and frequency 4 echo data are inverted to obtain $T_2$ distributions that are combined to obtain an apparent total porosity, capillary- and clay-bound water volumes, and other parameters of interest.

Focusing first on the determination of hydrocarbon volumes, in accordance with the present invention the method generally comprises four steps. First, the $T_2$'s of the hydrocarbons are determined. In the second step, the determined $T_2$'s are used to extract hydrocarbon signal amplitudes from two echo difference trains. In accordance with the present invention these amplitudes are used to compute $T_1$ values for the hydrocarbons, as shown below. Corrections for hydrogen index and polarization ($T_1$) are applied to the signal amplitudes in the last step to compute the hydrocarbon volumes. In the left processing branch, apparent total pore (or fluid) volume $\phi_{ta}$ is derived from the $T_{WL}$ and frequency 4 $T_2$ distributions. Corrected total pore volume $\phi_t$ is then computed as the sum of $\phi_{ta}$ and hydrocarbon volume corrections ($\Delta\phi_0$ and $\Delta\phi_g$) that are functions of the $T_1$'s and hydrogen indices of the hydrocarbon phases. An additional correction ($\Delta\phi_w$) may be required for under-polarized water, before various other parameters of interest are determined.

In particular, at step 30 of the method is formed the difference Edif1 between echo signals with a long wait time $T_{WL}$ and the first short wait time $T_{WS1}$. As shown in FIG. 1, in a preferred embodiment two or more measurements (data groups) associated with different frequencies can be combined (i.e., averaged) to result in a single data stream. Again with reference to FIG. 1, forming the difference Edif1 corresponds to forming differences between echo signals in the C and D data groups. It will be appreciated by those skilled in the art that the difference signal carries information essentially about the hydrocarbon phase which has a single $T_1$ and $T_2$ values, because the water contribution is canceled out. In the following step 40 is computed the $T_2$ spectrum of the Edif1 difference signal. Various ways of computing this spectrum are known in the art. In a preferred embodiment, one can use the MAP algorithm as disclosed in U.S. Pat. No. 5,517,115 to the assignee of the present application, or in Prammer, M. G.: "NMR Pore Size Distributions and Permeability at the Well Site," paper SPE 28368 presented at the 1994 SPE Annual Technical Conference and Exhibition, New Orleans, September 25–28. The contents of these publications are incorporated herein by reference.

In step 50 of the method are determined $T_2$ values for the corresponding hydrocarbon components from the $T_2$ spectrum of the difference signal. In a specific embodiment, this involves locating the peaks of the $T_2$ spectrum and assigning the values for the peak(s) as the $T_2$ values of the respective hydrogen components. It will be appreciated that relatively long $T_2$ peak values generally correspond to oil components, while relatively short $T_2$ values generally correspond to gas components.

Having determined the value(s) for the $T_2$ of the hydrocarbon components, in the following steps 60–90 the difference signals Edif1 and Edif2 are used to compute two apparent hydrocarbon volumes. In a preferred embodiment, this is done by using matched filters to fit exponential terms to each echo difference train. First, in step 80 is formed the Edif2 difference signal between the $T_{WL}$ and $T_{WS2}$ signals. With reference to FIG. 1 this corresponds to forming the difference between the A and B data groups. It will be appreciated that $T_{WS2}$ is longer than $T_{WS1}$.

Next the apparent hydrocarbon signal amplitudes (gas and/or oil), $A_0$, in the Edif1 and Edif2 echo difference trains are obtained by fitting the equation with matching filter, in this case $\exp(-t/T_{2mp})$, for gas and oil:

$$A(t) = A_0 e^{-\frac{t}{T_{2mp}}}, \quad (1)$$

where $A(t)$ represents the average echo difference amplitude at echo time t and $T_{mp}$ is the most probable amplitude $T_2$ value, determined from step 50 for a hydrocarbon zone, for the hydrocarbon phase component (gas or oil). On output, method steps 70 and 90 will give the two apparent hydrocarbon signal amplitudes $A_0$, corresponding to the two difference signals (Edif1 and Edif2).

Next, in step 100 of the method is determined the value for the $T_1$ parameter(s) for the hydrocarbon phases, using the following equation (separately for oil (phase p1) and gas (phase p2)):

$$\frac{e^{-\frac{T_{WS1}}{T_{1,p1,2}}} - e^{-\frac{T_{WL}}{T_{1,p1,2}}}}{e^{-\frac{T_{WS2}}{T_{1,p1,2}}} - e^{-\frac{T_{WL}}{T_{1,p1,2}}}} = \frac{A(T_{WS1}, T_{WL}, T_{1,p1,2})}{A(T_{WS2}, T_{WL}, T_{1,p1,2})} \quad (2)$$

where $A(T_{WS1}, T_{WL}, T_{1,p1,2})$ represents the apparent hydrocarbon amplitude from Edif1, and $A(T_{WS2}, T_{WL}, T_{1,p1,2})$ is the apparent hydrocarbon amplitude from Edif2. In the case when there is only one hydrocarbon phase, Eqn. (2) above reduces to:

$$\frac{e^{-\frac{T_{WS1}}{T_{1,p1}}} - e^{-\frac{T_{WL}}{T_{1,p1}}}}{e^{-\frac{T_{WS2}}{T_{1,p1}}} - e^{-\frac{T_{WL}}{T_{1,p1}}}} = \frac{A(T_{WS1}, T_{WL}, T_{1,p1})}{A(T_{WS2}, T_{WL}, T_{1,p1})} \quad (3)$$

The $T_1$'s from the triple-wait-time experiments are found by solving Eqn. (2) or Eqn. (3) when $A(T_{WS1}, T_{WL}, T_{1,pi})$ and $A(T_{WS2}, T_{WL}, T_{1,pi})$ are replaced with the Edif1 and Edif2 signal amplitudes, respectively, for each experiment. The most probable value for $T_{1mp}$ in a hydrocarbon zone of formation, is then used in step 110 to compute corrected hydrocarbon volumes $\phi_h$. In a preferred embodiment this is done by applying $$\phi_h = \frac{A_{o,Edif}}{HI_h \left( e^{-\frac{TWS1}{T_{1mp}}} - e^{-\frac{TWL}{T_{1mp}}} \right)} \quad (4)$$

where $HI_h$ is the hydrogen index of the hydrocarbon phase. In a specific embodiment, the most probable value $T_{1mp}$ is found as average over a number M of experiments, where for example, M=30 which corresponds to data points acquired in a hydrocarbon zone of formation. It will be appreciated that in alternative embodiments the hydrogen index correction can be obtained using different methods from the known parameters.

Turning next to the left branch of the processing algorithm illustrated in FIG. 2, in step 120 is determined the total apparent porosity $\phi_{ta}$, using $T_{WL}$ and frequency 4 $T_2$ distributions. In a specific embodiment, the determination is done by combining a long $T_W$ (i.e., data group A and/or C) and frequency 4 echo data (data group E). In a specific embodiment, the combination is done by separately computing the $T_2$ spectra of the two echo signals and generating a composite signal where below certain limit, i.e., 4 ms, data group E is used, while above that merge point the $T_{WL}$ distribution is applied. In alternative preferred embodiment, the combination is done entirely in the time domain, as described in U.S. Provisional Application No. 60/098,596, filed Aug. 31, 1998 to the assignee of the present application. The content of this application is incorporated herein by reference.

In the following step 130 the total porosity $\phi_t$ is computed from the total apparent porosity $\phi_{ta}$, and corrections for HI and polarization of water and hydrocarbons based on the apparent fluid volumes and $T_1$s computed in the right processing branch. In a specific embodiment, corrected total porosity is obtained using the corrections in Eqn. (4). Thus, for example, oil and gas corrections can be computed in a specific embodiment by $\phi_h*\exp(-T_{WL}/T_{1mp})$. In certain instances correction for under-polarized water can be computed as a fluid phase in the right branch of the algorithm. Alternative corrections for water can be applied as known in the art.

In the following step 140 is determined the total water volume as the difference between the total porosity and the total hydrocarbon volume. From the quantities determined thus far, in the final step 150 of the algorithm are computed various parameters of interest, as shown in a specific embodiment in FIG. 2.

The data processing method illustrated in FIG. 2 is a preferred embodiment designed to operate with the data acquisition sequence in FIG. 1. Alternative embodiments are possible and will be apparent to persons of skill in the art. For example, the individual steps discussed above can be implemented using alternative signal models and/or approaches. Thus, the specific use of equations (1)–(4) is not required in accordance with the present invention. For example, once the water contribution is canceled out, in the right branch of the algorithm one may consider different signal models, with increased number of parameters for increased accuracy.

D. Examples

The application of the new method for determining the hydrocarbon $T_1$ values is next illustrated in the following two cases.

Case 1: A two-phase mixture, consisting of water and light oil (possibly oil filtrate) or water and gas.

Following echo train correction, two echo train differences, Edif1 and Edif2, are used to eliminate the broadly distributed water signal, Edif1=$T_{WL}-T_{WS1}$ (data group C minus group D) data and Edif2=$T_{WL}-T_{WS2}$ (A group minus B group) data. Next, Edif1 and Edif2 are used to compute two apparent hydrocarbon volumes by using matched filters to fit exponential terms to each echo difference train. The $T_1$ for the hydrocarbon phase $T_{1p31}$ is given by $$\frac{e^{-\frac{T_{WS1}}{T_{1,pl}}} - e^{-\frac{T_{WL}}{T_{1,pl}}}}{e^{-\frac{T_{WS2}}{T_{1,pl}}} - e^{-\frac{T_{WL}}{T_{1,pl}}}} = \frac{A(T_{WS1}, T_{WL}, T_{1,pl})}{A(T_{WS2}, T_{WL}, T_{1,pl})},$$

where $A(T_{WS1}, T_{WL}, T_{1,p1})$ represents the apparent hydrocarbon amplitude from Edif1, and $A(T_{WS2}, T_{WL}, T_{1,p1})$ is the apparent hydrocarbon amplitude from Edif2, see Eqn. (3) above. For known values of $T_{WL}$, $T_{WS1}$, $T_{WS2}$ and the apparent hydrocarbon amplitudes from Edif1 and Edif2, the parameter $T_1$ of the hydrocarbon phase can be determined readily.

Case 1: A three-phase mixture of water, light oil (or oil filtrate), and gas.

Matched-filter exponential fitting is performed on the Edif1 and Edif2 echo differences as above to obtain apparent volumes for each of the hydrocarbon phases. $T_1$'s for the hydrocarbon phases are given by applying Eqn. (2) separately for oil (phase p1) and gas (phase p2). As before, $T_1$ values for the hydrocarbons can be computed directly from the known quantities.

Based on the above discussion, it is apparent that a key element of the method for determining hydrocarbon $T_1$ values is the selection of the wait times. Generally, all $T_W$ values should be long enough to polarize the water signal fully, so that echo difference signals (i.e., Edif1, Edif2, . . . ) contain only hydrocarbon signals that have discrete $T_1$ and $T_2$ values for each phase. In addition, in accordance with the present invention the left side of Eqns. (2) and (3) must be from 1.4 to 5 for $T_1$ to be accurately determined. Moreover, the delay times must be chosen to keep the overall activation set cycle time as short as possible to maximize logging speed.

Figure 3:
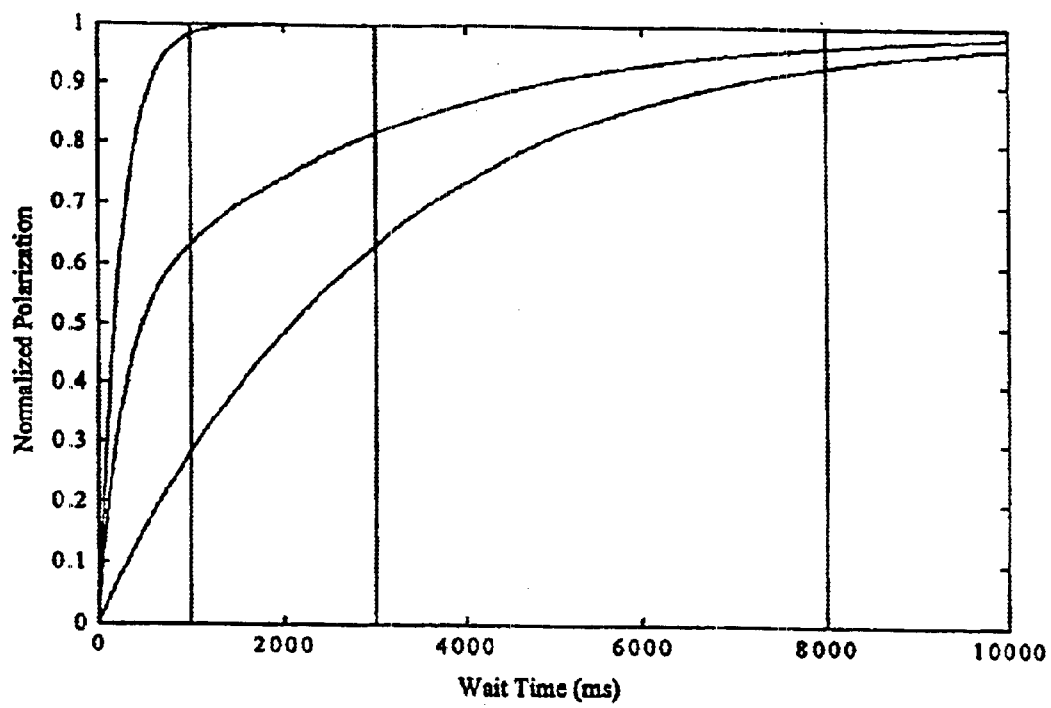
FIG. 3 is an illustration of hypothetical saturation recovery curves for water, hydrocarbon phase and a mixture of water and the hydrocarbon phase used in a specific embodiment of the present invention.
Figure 4:
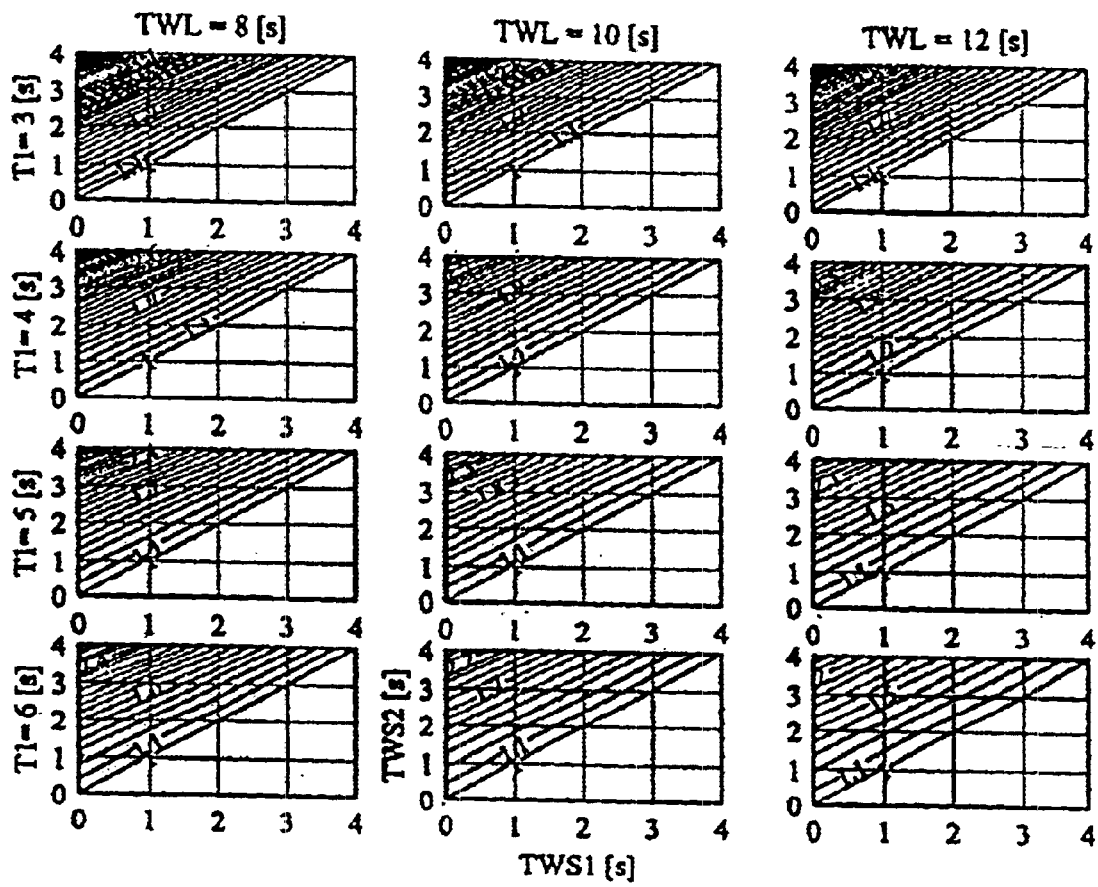
FIG. 4 are waiting time $T_{WS2}$–$T_{WS1}$ cross-plots that can be used in accordance with the present invention for the selection of optimum logging acquisition parameters.

In a typical Gulf of Mexico gas well, water $T_2$ signals range from a few hundred microseconds to a few hundred milliseconds, and gas $T_1$'s are on the order of a few seconds. See, e.g., Akkurt, R., et al: "NMR Logging of Natural Gas Reservoirs," Paper N presented at the $36^{th}$ Annual SPWLA Logging Symposium, Paris, Jun. 26–29, 1995. FIG. 3 shows hypothetical saturation recovery curves for water (assuming $T_1$=0.25 s) and hydrocarbon (assuming $T_1$=3 s). The uppermost curve is for water with an assumed $T_1$=0.25 s. From this, it can be seen that a $T_W$ of 1 second will achieve more than 95% polarization of the water signal. The bottom curve depicts a hydrocarbon phase ($T_1$=3 s). The middle curve represents an equal mixture of the water and hydrocarbon phases. For two-phase mixtures of these fluids, accurate values for hydrocarbon $T_1$ and volume can be obtained with the triple-wait-time method when wait times of 1, 3, and 8 seconds (indicated by the vertical lines) are used. Shown in FIG. 4 are crossplots of $T_{WS1}$ and $T_{WS2}$ with contour lines of $$F = [e^{-(T_{WS1}/T_1)} - e^{-(T_{WL}/T_1)}]/[e^{-(T_{WS2}/T_1)} - e^{-(T_{WL}/T_1)}] \quad (5)$$

for $T_1$ values from 3 to 6 seconds. The $T_{WS2}-T_{WS1}$ crossplots illustrate the selection of triple-wait-time combinations according to the method of the present invention dependent on expected hydrocarbon $T_1$ values (rows of panels) and long wait times, (columns of panels). Contour lines according to Eqn. (5) start at F=1 and increase by increments of 0.1 toward the upper left corner in each panel. For good hydrocarbon $T_1$ determinations, F should be 1.4 or larger. With reference to FIG. 4, if a 1-second $T_w$ ($T_{WS1}$) is needed to fully polarize the water signal and the possible hydrocarbon $T_1$ could be as large as 6 seconds, then for an 8-second $T_{WL}$ the charts suggest that $T_{WS2}$ should be 3 seconds.

In accordance with the present invention, these crossplots can be used in selecting the best wait-time combination for a given set of logging conditions. For example, based on the above criteria and the information in FIGS. 3 and 4, the three $T_W$ values for a typical Gulf of Mexico well can be selected as 1, 3, and 8 seconds. It should be apparent that for different conditions different $T_W$ can be selected using the crossplots shown in FIG. 4, or the mathematical relationship expressed in Eqn. (5). The derivation of these tools is believed to be a significant contribution of the present invention.

E. Applications

One of the main applications of the system and method of this invention stems from the need to determine accurately the $T_1$ parameter corresponding to slow $T_2$ decay components in echo difference signals usually associated with light hydrocarbons, such as light oil, oil filtrate, and gas or free brine in large pores. Three experiments were performed with mixtures of $C_{12}H_{26}$ and doped water, a sandstone core filled with water and $C_{12}H_{26}$, and a freshwater-filled tank to demonstrate the effectiveness of the proposed method. A MARAN-1 laboratory spectrometer operating at a 1-MHz resonant frequency was used to obtain measurements on the bulk $C_{12}H_{26}$/doped water and sandstone core samples. A MRIL-Prime logging tool was used to perform experiments in a water-filled tank. The following describes the procedures and results obtained from each experiment.

Mixture of Doped Water and Dodecane.

A 3.5-in. (inside diameter) glass sample holder was used to measure bulk fluids in the MARAN spectrometer. To determine the true volumes of the samples in arbitrary units, CPMG pulse sequences were used to make 10 measurements on separate samples of doped water and $C_{12}H_{26}$. The mean volume of the doped water sample was determined to be 136±0.7 arbitrary units. Similarly, the mean volume for the $C_{12}H_{26}$ sample was found to be 108±0.9 arbitrary units. Inversion recovery measurements, consisting of 51 inversion recovery times, were performed separately on the samples. The data from these experiments were used to find bulk-fluid $T_1$ values of 395±1.8 and 995±4.7 ms, respectively, for the doped water and $C_{12}H_{26}$ samples.

The samples of doped water and $C_{12}H_{26}$ were combined and mixed to form a 1.26:1-volume ratio of doped water to $C_{12}H_{26}$. A series of tests were performed on the mixture in which different wait-time combinations were used to collect sets of 30 CPMG triple-wait-time experiments consisting of 5,000 1-ms echoes. Data from these tests were used to derive the $C_{12}H_{26}$ volumes and $T_1$'s that are shown in Table 1 below for each triple-wait-time combination trial. By comparing the true values with the results in Table 1, the smallest error occurred when a triple-wait-time combination of 1, 2, and 8 seconds was used.

TABLE 1

Optimization of $T_w$s for determining $T_1$ and volume of hydrocarbon in a mixture of dodecane and doped water

| | True values | TWs = 1, 1.5, & 8 s | TWs = 1, 2, & 8 s | TWs = 1, 2.5, & 8 s | TWs = 1, 3, & 8 s |
|---|---|---|---|---|---|
| $T_1$ of $C_{12}H_{26}$ (ms) | 995[a] | 1162 | 991 | 1047 | 893 |
| Standard dev. of $T_1$ (ms) | 4.7 | 158.1 | 66.4 | 74.2 | 150.9 |
| Volume of $C_{12}H_{26}$ (arb.) | 108[b] | 92.9[c] | 106.7[c] | 102[c] | 119.5[c] |
| Standard dev. of the volume (arb.) | 0.9 | 3.3 | 4.0 | 4.1 | 7.1 |

[a]True $T_1$ was derived from an inversion recovery measurement with 51 inversion recovery times performed on a bulk sample.
[b]Reported sample volume is the average signal amplitude at t = 0 obtained from $T_2$ inversions performed on 10 CPMG measurements.
[c]The volume of $C_{12}H_{26}$ in the doped water/$C_{12}H_{26}$ mixture is the same as the $C_{12}H_{26}$ sample.

Figure 5:
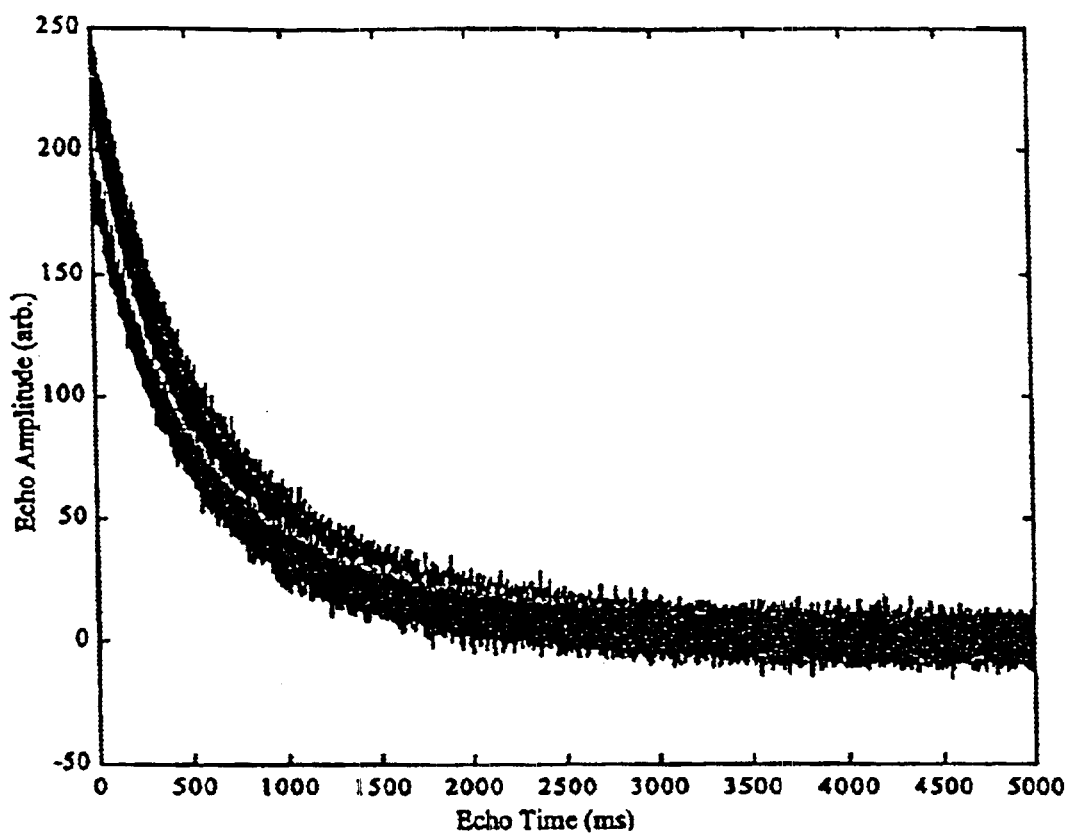
FIG. 5 is an overlay of triple-wait-time echo trains obtained from CPMG experiments performed in experiments performed on a 1.26:1 mixture of doped water and $C_{12}H_{26}$ for different $T_W$.

FIG. 5 shows the triple-wait-time echo trains acquired for the 1-, 2-, and 8-second combination. The MAP algorithm was used to perform 21-bin $T_2$ inversions of the, 8-second wait-time echo trains. Overlay of triple-wait-time echo trains obtained in the laboratory from 30 CPMG experiments performed on a 1.26:1 mixture of doped water and $C_{12}H_{26}$. The top set of curves is the 8-second $T_W$. The middle set is the 2-second $T_W$. The bottom set of curves was acquired with a 1-second $T_W$. For details of the MAP algorithm the reader is directed to U.S. Pat. No. 5,517,115; and Prammer, M. G.: "NMR Pore Size Distributions and Permeability at the Well Site," paper SPE 28368 presented at the 1994 SPE Annual Technical Conference and Exhibition, New Orleans, September 25–28, the disclosure of which is hereby incorporated by reference.

Figure 6:
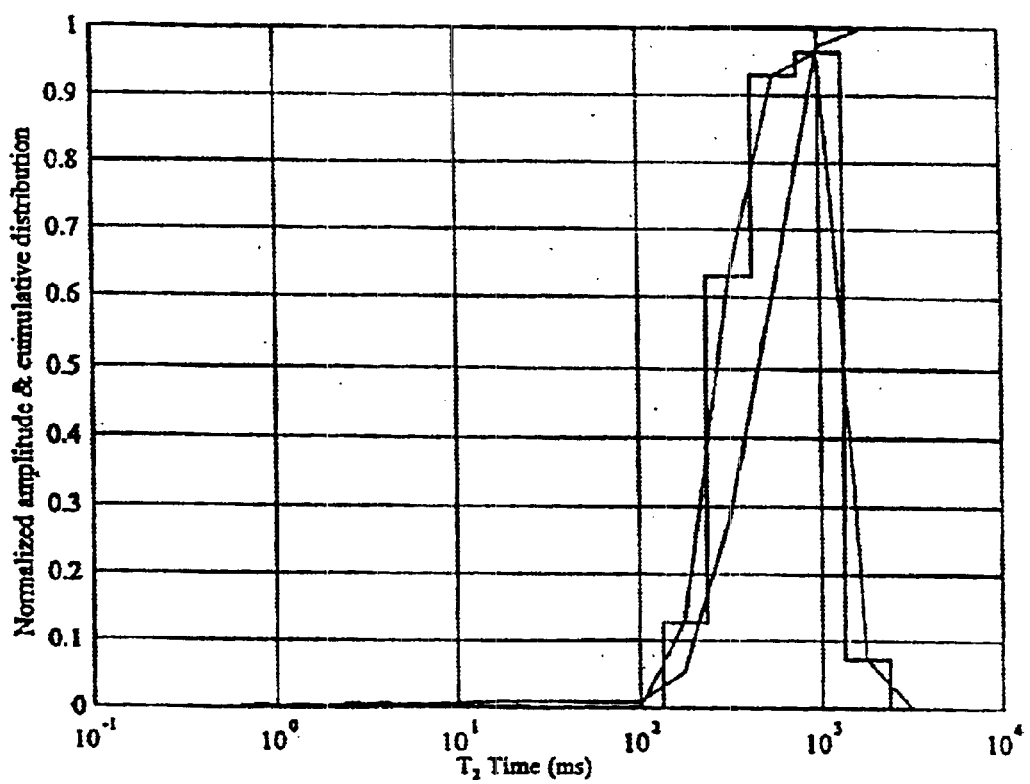
FIG. 6 is a $T_2$ distribution, selected at random, from one of the 8-s $T_W$ CPMG experiments performed on a doped-water/$C_{12}H_{26}$ mixture.

An example from one experiment, FIG. 6 shows a unimodal distribution of $T_2$ values. This $T_2$ distribution was selected at random from one of the 8-s $T_W$ CPMG experiments performed on the doped-water/$C_{12}H_{26}$ mixture using this invention. A MAP inversion with 21 $T_2$ bins (indicated by the stair-step curve) was performed. The bin amplitudes, shown as the line joining $T_2$ times at the bin centers, have been normalized to the maximum bin amplitude. The dotted curve indicates the normalized cumulative amplitude as a function of $T_2$ time. The two liquid phases are not resolved in the $T_2$ spectrum at the signal-to-noise conditions for the single experiment shown. A similar situation occurs in many logging applications, which can make fluid typing difficult with only one kind of NMR acquisition.

Figure 7:
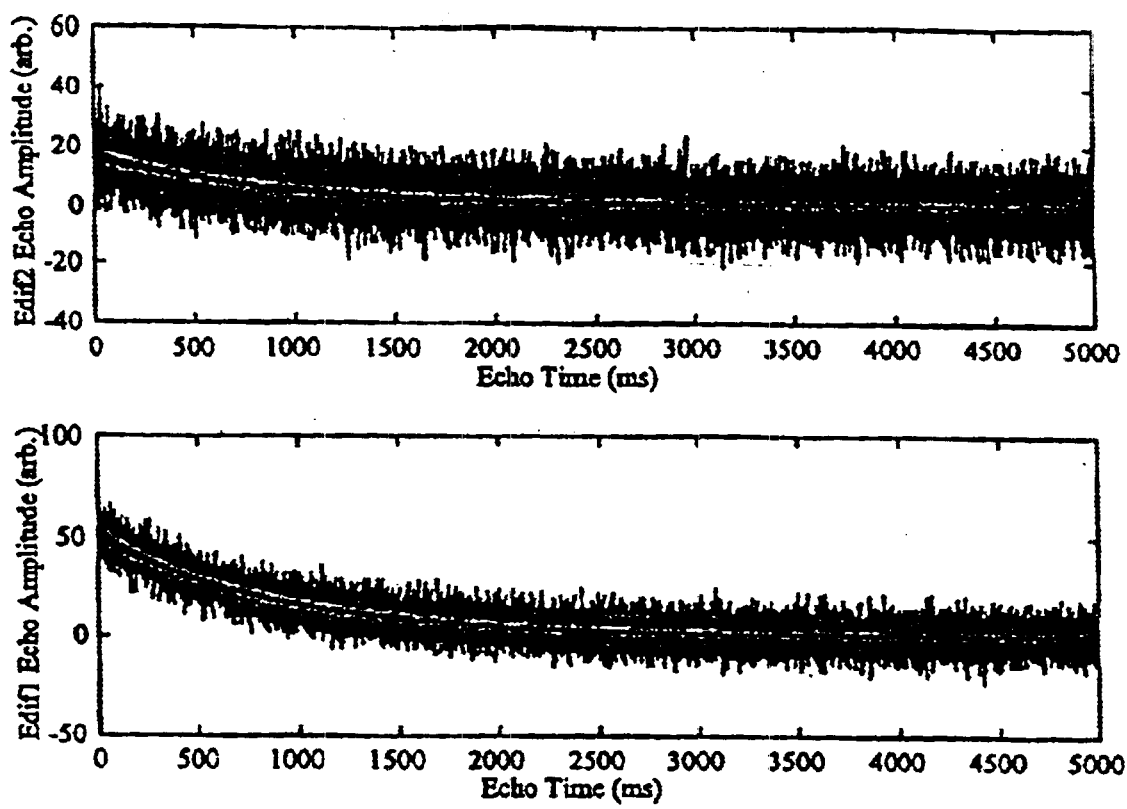
FIG. 7 shows overlays of difference echo trains for 30 CPMG triple-wait-time sequences performed on a doped-water/$C_{12}H_{26}$ mixture using the method of the present invention.

To obtain only $C_{12}H_{26}$ signals, the triple-wait-time echo trains were used to generate two sets of echo train differences for each experiment, shown in FIG. 7. FIG. 7 shows overlays of difference echo trains for the 30 CPMG triple-wait-time sequences performed on a doped-water/$C_{12}H_{26}$ mixture. The top panel shows the Edif2 (8-second minus 2-second) differences and the bottom panel shows the Edif1 (8-second–1-second). In addition, each panel includes the corresponding matched-filter fitted curves that provided the apparent $C_{12}H_{26}$ volume for each experiment.

Assuming the doped water signals are eliminated in the Edif1 (8-second minus 1-second echo difference) echo train, Edif1 was used to determine the most probable hydrocarbon $T_2$ value–$T_{2mp}$. The value was found by performing $T_2$ inversions on each Edif1 echo train and computing the average of the largest $T_2$ modes observed in the 30 distributions.

Apparent $C_{12}H_{26}$ signal amplitudes, $A_0$, in the echo difference trains were obtained for each experiment by fitting the Eqn. (1), reproduced here for convenience $$A(t) = A_o e^{-\frac{t}{T_{2mp}}},$$

where A(t) represents the average echo difference amplitude at echo time t to both Edif1 and Edif2.

The apparent $T_1$'s from the triple-wait-time experiments were found by solving Eq. 1 when $A(T_{WS1}, T_{WL}, T_{1,p1})$ and $A(T_{WS2}, T_{WL}, T_{1,p1})$ were replaced with the Edif1 and Edif2 $C_{12}H_{26}$ signal amplitudes, respectively, for each experiment. The most probable $T_1$ (average of the 30 experiments), $T_{1mp}$, was then used to compute corrected hydrocarbon volumes $(C_{12}H_{26})$ $\phi_h$ by applying Eqn. (4)

$$\phi_h = \frac{A_{o,Edif1}}{HI_h\left(e^{-\frac{TWS1}{T_{1mp}}} - e^{-\frac{TWL}{T_{1mp}}}\right)},$$

where $HI_h$ is the hydrogen index of the hydrocarbon, which is equal to 1 for $C_{12}H_{26}$. The average $T_1$ and its standard deviation along with the average corrected volume and its standard deviation are given in Table 1 above. For the 1, 2, and 8-second wait-time combination, the absolute error for $T_1$ is 0.4%, and the absolute error for the volume of $C_{12}H_{26}$ is 1.2%.

Sandstone Core Filled With Water and Dodecane.

A three-step process was used to prepare 3.5-(diameter) by 4.5-in. sandstone core having 22.06% porosity for laboratory NMR experiments with water and $C_{12}H_{26}$ pore fluids. The core was cleaned and saturated with a 4% potassium chloride (KCl) brine solution under 1 atmosphere of pressure. Then the sample was desaturated to a capillary pressure of 50 psi, and the brine volume in the core was decreased from 151.9 to 32.4 cm³. Under atmospheric conditions, 119.5 cm³ of $C_{12}H_{26}$ were added to the sample, and the core was placed in a closed glass sample holder before making NMR measurements.

As before, several triple-wait-time combinations were investigated to determine the best set of wait times for the saturation state. Sets of 28 triple-wait-time CPMG pulse sequences were collected, which consisted of 9,000 0.4-ms echoes, for each wait-time combination. Data from these tests were used to derive the $C_{12}H_{26}$ volumes and $T_1$'s that are shown in Table 2 for each wait-time combination tried. The true $C_{12}H_{26}$ $T_1$ value for these experiments was taken to be the same as the value determined in the bulk fluid experiments, and true $C_{12}H_{26}$ volume was normalized to core porosity. By comparing the true values with the results in Table 2, the smallest error occurred when a triple-wait-time combination of 0.4, 1, and 6 seconds was used.

TABLE 2

Optimization of $T_w$s for determining $T_1$ and volume of hydrocarbon in a sandstone core filled with water and dodecane

|  | True values | TWs = 0.4, 0.8 & 6 s | TWs = 0.4, 1 & 6 s | TWs = 0.4, 1.2, & 6 s | TWs = 0.4, 1.4, & 6 s |
|---|---|---|---|---|---|
| $T_1$ of $C_{12}H_{26}$ (ms) | 995[a] | 1149 | 1050 | 1157 | 1162 |
| Standard dev. of $T_1$ (ms) | 4.7 | 12.5 | 12.0 | 11.6 | 10.5 |
| Volume of $C_{12}H_{26}$ (arb.) | 17.35[d] | 17.09 | 17.10 | 16.97 | 17.02 |
| Standard dev. of the volume (arb.) | 0.140 | 0.060 | 0.060 | 0.061 | 0.073 |

[a]True $T_1$ was derived from an inversion recovery measurement with 51 inversion recovery times performed on a bulk sample.
[d]Actual $C_{12}H_{26}$ volume = $C_{12}H_{26}$ saturation × core porosity.

Figure 8:
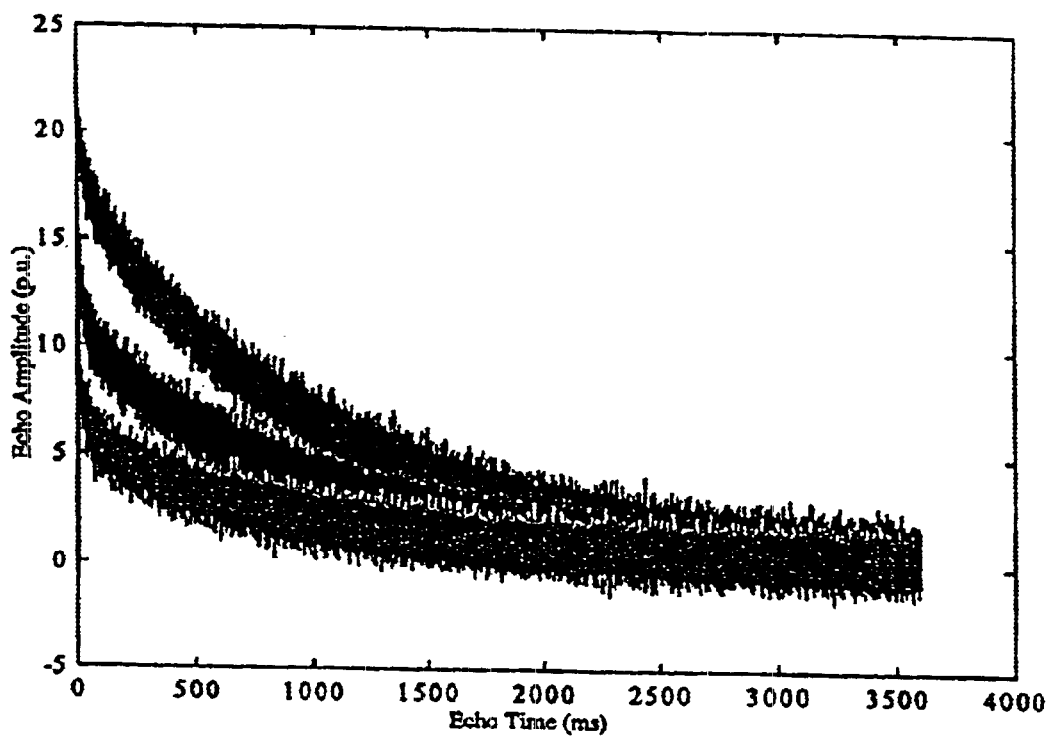
FIG. 8 is overlay of triple-wait-time echo trains obtained in accordance with the present invention in a laboratory setting from 28 CPMG experiments performed on a 22-p.u. sandstone core filled with a 4% KCl brine and $C_{12}H_{26}$.

The triple-wait-time echo trains acquired with the 0.4-, 1-, and 6-second combination are displayed in FIG. 8. The figure shows overlay of triple-wait-time echo trains obtained in the laboratory from 28 CPMG experiments performed on a 22-p.u. sandstone core filled with a 4% KCl brine and $C_{12}H_{26}$. The top set of curves is the 6-second $T_W$. The middle set is the 1-second $T_W$. The bottom set of curves was acquired with a 0.4-second $T_W$.

Figure 9:
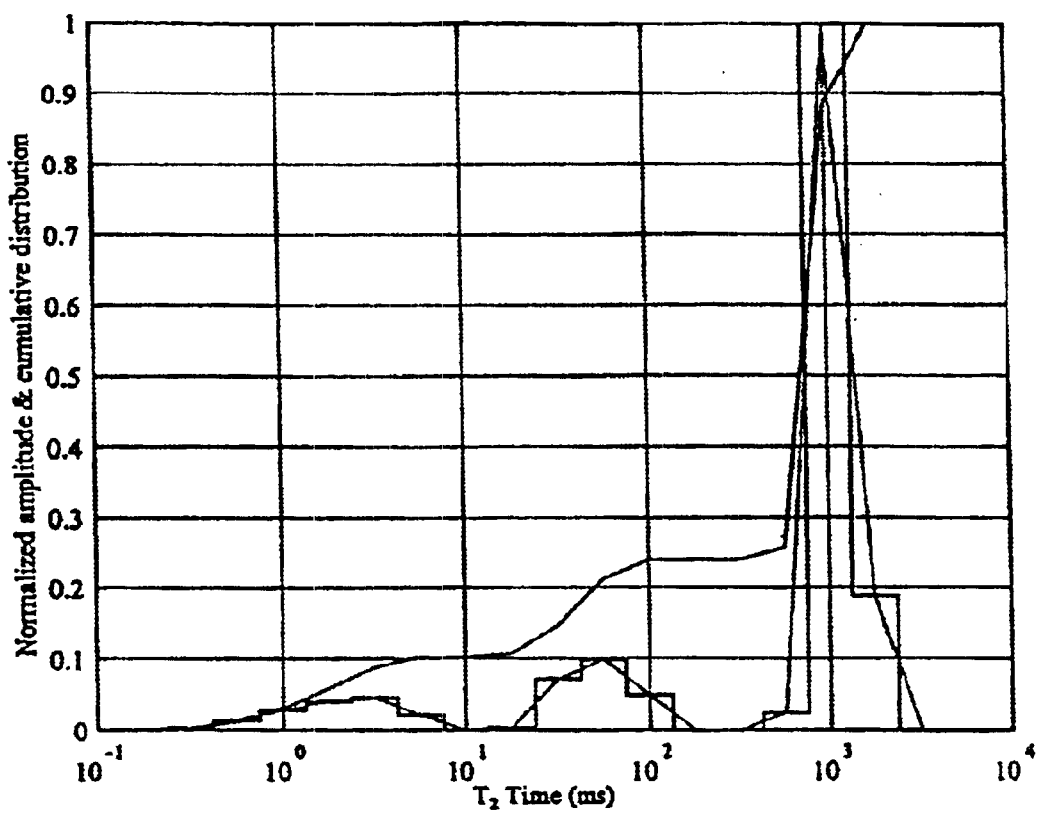
FIG. 9 is a $T_2$ distribution from a 6-s $T_w$ measurement performed on the brine- and $C_{12}H_{26}$-filled sandstone core in accordance with the present invention.

FIG. 9 shows the results of a 21-bin inversion performed on one of the 6-second $T_W$ echo trains. The figure illustrates a $T_2$ distribution, selected at random, from one of the 6-s $T_W$ measurements performed on the brine- and $C_{12}H_{26}$-filled sandstone core. The sharp, high-amplitude peak in the 1,000-ms bin comes from the $C_{12}H_{26}$. The two lower amplitude peaks to the left are from the residual brine. The cumulative amplitude ratio (dotted curve) indicates that the volume ratio of $C_{12}H_{26}$ to water is approximately 4:1, close to the materials balance ratio of 3.7:1.

Figure 10:
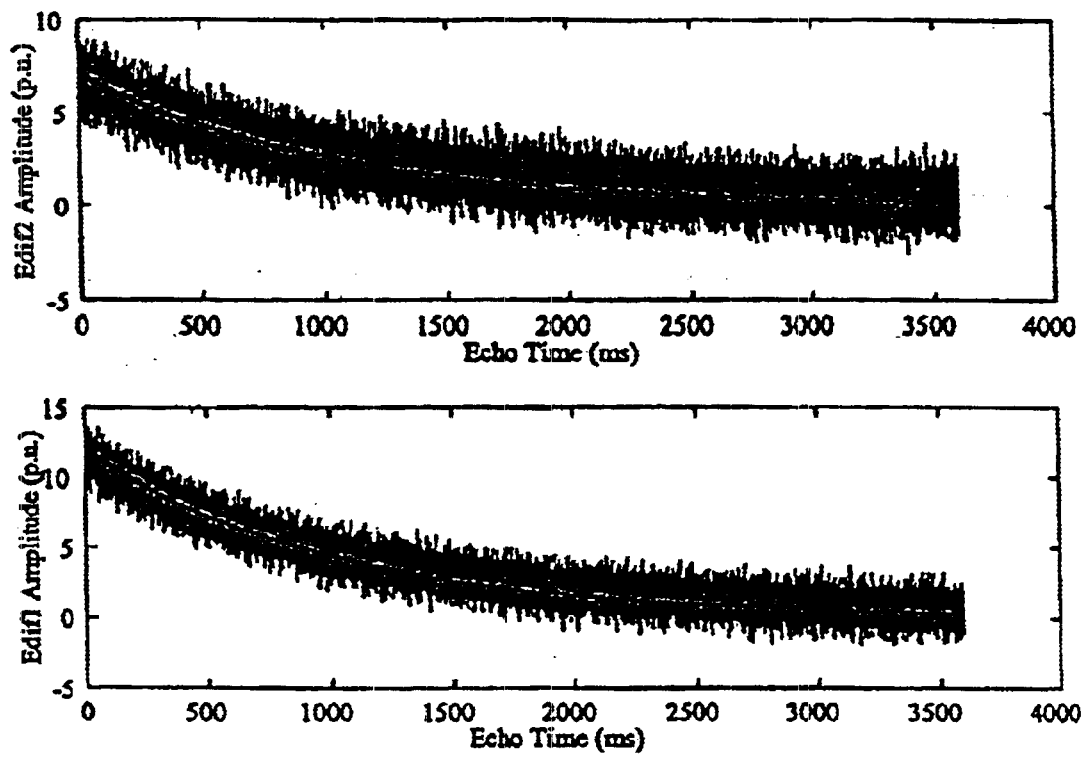
FIG. 10 shows overlays of difference echo trains for 28 CPMG triple-wait-time sequences performed on the brine- and $C_{12}H_{26}$-filled sandstone core sample, along with matched-filter curves.

Edif1 and Edif2 echo differences (shown in FIG. 10) were generated from the triple-wait-time echo trains to cancel the residual water signal. The most probable hydrocarbon $T_2$ was extracted by inverting the Edif1 (6-second minus 0.4-second echo difference) echo trains. More specifically, FIG. 10 shows overlays of difference echo trains for the 28 CPMG triple-wait-time sequences performed on the brine- and $C_{12}H_{26}$-filled sandstone core sample. The top panel shows the Edif2 (6-second minus 1-second) differences. The bottom panel shows the Edif1 (6-second minus 0.4-second). Matched-filter fitted curves are also shown for each experiment that provided the apparent $C_{12}H_{26}$ volume.

Edif1 and Edif2 were each fit to the exponential relationship in Eq. (1) to obtain the apparent $C_{12}H_{26}$ signal amplitudes that were used in Eq. (3) to compute an apparent $T_1$ for each CPMG triple-wait-time sequence. Eq. (4) was then used to compute corrected $C_{12}H_{26}$ volumes for comparison with the true value. The absolute error for $T_1$ is 5.5%, and the absolute error for the volume of $C_{12}H_{26}$ is 1.4%. The Edif1 signal-to-noise ratio is defined for the examples in this paper as the first echo difference amplitude divided by the standard deviation of the mean of the last 100 echo difference amplitudes. Edif1 signal-to-noise ratio was approximately 5:1 in this series of experiments, compared with the 7:1 ratio obtained during the bulk fluid mixture experiments discussed previously. The larger errors obtained in this case are attributed to the poorer signal-to-noise quality of the measurements.

Freshwater Tank.

The triple-wait-time method was also tested by the use of an MRIL-Prime tool in a freshwater-filled tank in which the water has a volume of 100 porosity units (p.u.) and a $T_1$ of approximately 2.5 seconds.

Again, several wait-time combinations were tried. The activation set shown in FIG. 1 was used to acquire 48 sets of CPMG pulse sequences in the water tank for each wait time combination. In all but frequency 4, the collected echo trains consisted of 400 1.2-ms echoes. Table 3 lists the $T_1$ and volume results from each test, which show that the optimum combination of wait times for this setup is 1, 3, and 10 seconds.

TABLE 3

Optimization of $T_w$s for determining $T_1$ and volume of free fresh water in a water tank

|  | True values | TWs = 1, 3, & 10 s | TWs = 2, 3 & 10 s | TWs = 1, 3.5, & 12 s | TWs = 1.5, 3.5, & 6 s |
|---|---|---|---|---|---|
| $T_1$ of fresh water (ms) | ~2500[e] | 2180 | 2010 | 2059 | 2018 |
| Standard dev. of $T_1$ (ms) |  | 176.2 | 394.2 | 170.0 | 216.2 |
| Volume of $C_{12}H_{26}$ (arb.) | 100 | 100.4 | 99.6 | 102 | 102 |
| Standard dev. of the volume (arb.) |  | 2.43 | 4.35 | 2.81 | 3.13 |

[e]The true $T_1$ and the volume of the water were obtained in a water tank used to calibrate MRIL-Prime tools.

Though an accurate water volume was obtained from the series of experiments, the water $T_1$ value obtained with the triple-wait-time method had a relatively large absolute error of 15%. It is believed that the acquisition time of 0.48 seconds (400 echoes×1.2 ms/echo), which is short compared with the $T_2$ of bulk water and the 4:1 Edif1 signal-to-noise ratio, contributed substantially to this error.

The activation set outlined in FIG. 1, however, has an important advantage over dual-frequency, dual-$T_W$ activations. (See Akkurt, R., et al: "NMR Logging of Natural Gas Reservoirs," Paper N presented at the 36$^{th}$ Annual SPWLA Logging Symposium, Paris, Jun. 26–29, 1995). Because four frequencies are available to collect Edif1 echo-difference data, the signal-to-noise quality is 1.4 times better compared with the same data acquired with a dual-frequency activation.

Figure 11:
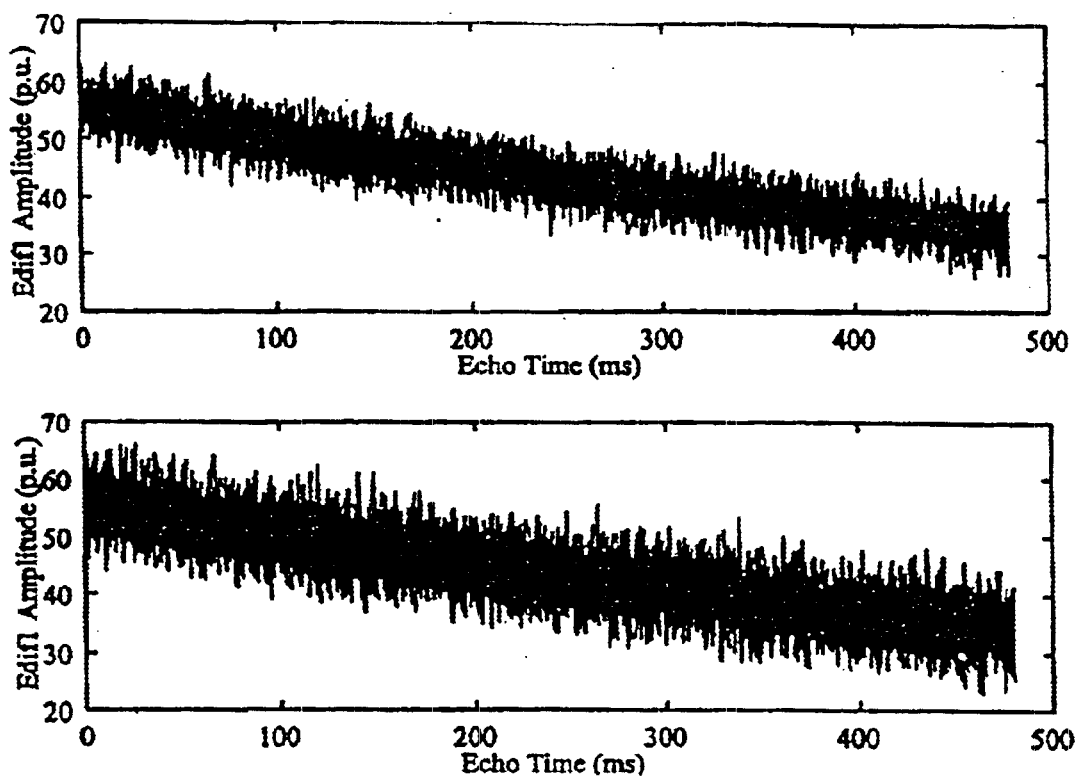
FIG. 11 illustrates an improvement in signal-to-noise ratio of Edif1 echo differences using the multifrequency triple-wait-time acquisition method of the present invention, compared with those obtained with a dual-$T_w$, dual frequency method.

Specifically, FIG. 11 shows how the multifrequency triple-wait-time acquisition method, developed for the MRIL-Prime tool, improves the signal-to-noise ratio of Edif1 echo differences compared with those obtained with a dual-$T_W$, dual frequency method. The examples shown were obtained in a freshwater-filled calibration tank. The MRIL-Prime Edif1 difference echo trains are displayed in the top panel. The dual-$T_W$ dual frequency Edif1 appears in the bottom panel. The multifrequency triple-wait-time method gives an echo difference signal-to-noise ratio that is 1.4 times better. The increase in Edif1 signal-to-noise ratio, shown in FIG. 11, is important because it influences the accuracy of $T_2$'s, $T_1$'s, and volumes of hydrocarbons (or free brine) derived from multi-wait-time measurements.

Based on the above, the inventors have found that the proposed data acquisition and processing method result in substantial improvements over prior art methods. Thus, for NMR signal differences having signal-to-noise ratios larger than 4:1, the absolute errors in determining fluid volume were less than 1.5%. In general, the new acquisition method brings a 1.4-time improvement to echo difference signal-to-noise ratios compared with previous implementations of dual-$T_W$ logging with dual-frequency tools. The triple-wait-time technique has been applied successfully to two-phase or three-phase mixtures of water and hydrocarbons—light oil (or oil filtrate) and gas.

Mathematical Foundations

The following provides the mathematical foundation for the method outlined above. The time-dependent NMR $T_2$ signal for a three-phase mixture of oil, gas, and water in a water-wet formation can be expressed as a weighted sum of exponential terms $$A(t, T_W) = HI_g\left(1 - e^{-\frac{T_W}{T_{1g}}}\right)\sum_i P_g(T_2(i))e^{-\frac{t}{T_{2(i)}}} + \quad (A\text{-}1)$$

$$HI_o\left(1 - e^{-\frac{T_W}{T_{1o}}}\right)\sum_i P_o(T_2(i))e^{-\frac{t}{T_{2(i)}}} +$$

$$\sum_i P_w(T_2(i))\left(1 - e^{-\frac{T_W}{T_{1w}(i)}}\right)e^{-\frac{t}{T_{2(i)}}}$$

where $P_g(T_2)$, $P_o(T_2)$, $P_w(T_2)$ are the $T_2$ incremental porosity spectra of gas, oil and water, respectively. For water, $T_1$ and $T_2$ are assumed to be linked through a constant ratio. See, e.g., Kleinberg, R. L., et al.: "Nuclear Magnetic Resonance of Rocks: $T_1$ vs $T_2$," paper SPE 26470 presented at the 1993 SPE Annual Technical Conference and Exhibition, Houston, October 3–6. Therefore, the index of $T_{1w}$ is correlated with $T_2$. If the hydrocarbon signals are limited to singular $T_2$ times, then Equation A-1 simplifies to $$A(t, T_W) = HI_g\left(1 - e^{-\frac{T_W}{T_{1g}}}\right)\phi_g e^{-\frac{t}{T_{2g}}} + \quad (A\text{-}2)$$

$$HI_o\left(1 - e^{-\frac{T_W}{T_{1o}}}\right)\phi_o e^{-\frac{t}{T_{2o}}} +$$

$$\sum_i P_w(T_2(i))\left(1 - e^{-\frac{T_W}{T_{1w}(i)}}\right)e^{-\frac{t}{T_{2(i)}}}$$

For triple-wait-time method, three similar equations can be used to represent time-dependent signal amplitudes in which the actual wait times are substituted $T_W$ $$A(t, T_{WL}) = HI_g\left(1 - e^{-\frac{T_{WL}}{T_{1g}}}\right)\phi_g e^{-\frac{t}{T_{2g}}} + \quad (A\text{-}3)$$

$$HI_o\left(1 - e^{-\frac{T_{WL}}{T_{1o}}}\right)\phi_o e^{-\frac{t}{T_{2o}}} +$$

$$\sum_i P_w(T_2(i))\left(1 - e^{-\frac{T_{WL}}{T_{1w}(i)}}\right)e^{-\frac{t}{T_{2(i)}}}$$

$$A(t, T_{WS1}) = HI_g\left(1 - e^{-\frac{T_{WS1}}{T_{1g}}}\right)\phi_g e^{-\frac{t}{T_{2g}}} + \quad (A\text{-}4)$$

$$HI_o\left(1 - e^{-\frac{T_{WS1}}{T_{1o}}}\right)\phi_o e^{-\frac{t}{T_{2o}}} +$$

$$\sum_i P_w(T_2(i))\left(1 - e^{-\frac{T_{WS1}}{T_{1w}(i)}}\right)e^{-\frac{t}{T_{2(i)}}}$$

$$A(t, T_{WS2}) = HI_g\left(1 - e^{-\frac{T_{WS2}}{T_{1g}}}\right)\phi_g e^{-\frac{t}{T_{2g}}} + \quad (A\text{-}5)$$

$$HI_o\left(1 - e^{-\frac{T_{WS2}}{T_{1o}}}\right)\phi_o e^{-\frac{t}{T_{2o}}} +$$

$$\sum_i P_w(T_2(i))\left(1 - e^{-\frac{T_{WS2}}{T_{1w}(i)}}\right)e^{-\frac{t}{T_{2(i)}}}$$

Models of the time-dependent signals in the Edif1 and Edif2 echo difference trains are obtained when Eqs. A-4 and A-5 are subtracted from Eq. A-3, $$Edif1(t) = HI_g\phi_g\left(e^{-\frac{T_{WS1}}{T_{1g}}} - e^{-\frac{T_{WL}}{T_{1g}}}\right)e^{-\frac{t}{T_{2g}}} + \quad (A\text{-}6)$$

$$HI_o\phi_o\left(e^{-\frac{T_{WS1}}{T_{1o}}} - e^{-\frac{T_{WL}}{T_{1o}}}\right)e^{-\frac{t}{T_{2o}}} +$$

$$\sum_i P_w(T_2(i))\left(e^{-\frac{T_{WS1}}{T_{1w}(i)}} - e^{-\frac{T_{WL}}{T_{1w}(i)}}\right)e^{-\frac{t}{T_{2(i)}}}$$

$$Edif2(t) = HI_g\phi_g\left(e^{-\frac{T_{WS2}}{T_{1g}}} - e^{-\frac{T_{WL}}{T_{1g}}}\right)e^{-\frac{t}{T_{2g}}} + \quad (A\text{-}7)$$

$$HI_o\phi_o\left(e^{-\frac{T_{WS2}}{T_{1o}}} - e^{-\frac{T_{WL}}{T_{1o}}}\right)e^{-\frac{t}{T_{2o}}} +$$

$$\sum_i P_w(T_2(i))\left(e^{-\frac{T_{WS2}}{T_{1w}(i)}} - e^{-\frac{T_{WL}}{T_{1w}(i)}}\right)e^{-\frac{t}{T_{2(i)}}}$$

When $T_{WS1}$ is much larger than the maximum water $T_1$ value, then contributions to Edif1 and Edif2 from under-polarized water become negligible and the last term in Eqs. A-6 and A-7 disappears. The product of hydrogen index, hydrocarbon porosity, and the differential polarization factor represents the amplitude of the hydrocarbon signal. Thus, Eqs. A-6 and A-7 simplify to bi-exponential equations $$Edif1(t) = A_g(T_{WS1}, T_{WL}, T_{1g})e^{-\frac{t}{T_{2g}}} + A_o(T_{WS1}, T_{WL}, T_{1g})e^{-\frac{t}{T_{2o}}} \quad (A-8)$$

$$Edif2(t) = A_g(T_{WS2}, T_{WL}, T_{1g})e^{-\frac{t}{T_{2g}}} + A_o(T_{WS2}, T_{WL}, T_{1g})e^{-\frac{t}{T_{2o}}} \quad (A-9)$$

The hydrocarbon signal amplitudes in the Edif1 and Edif2 difference echo trains models can be obtained by applying matched-filter exponential fitting. Once the amplitudes have been determined for the two echo difference trains, the hydrocarbon $T_1$'s can be calculated by taking their ratio. The hydrocarbon index and hydrocarbon porosity are canceled when the amplitude ratio is computed so that, for either hydrocarbon phase:

$$\frac{A_h(T_{WS1}, T_{WL}, T_{1h})}{A_h(T_{WS2}, T_{WL}, T_{1h})} = \frac{e^{-\frac{T_{WS1}}{T_{1h}}} - e^{-\frac{T_{WL}}{T_{1h}}}}{e^{-\frac{T_{WS2}}{T_{1h}}} - e^{-\frac{T_{WL}}{T_{1h}}}} \quad (A-10)$$

For the reader's convenience, a list of all notations used in the description above is given next.

| Nomenclature | |
| --- | --- |
| A | amplitude, p.u. |
| D | self-diffusion coefficient, cm²/s |
| Edif1 | echo train difference from $T_{WL}$ and $T_{WS1}$ data, p.u. |
| Edif2 | echo train difference from $T_{WL}$ and $T_{WS2}$ data, p.u. |
| F | contour constant |
| HI | hydrogen index |
| P | incremental porosity |
| t | time, s |
| $T_1$ | longitudinal NMR relaxation time, s |
| $T_2$ | transverse NMR relaxation time, s |
| $T_e$ | echo spacing, ms |
| $T_w$ | wait-time, s |
| $T_{WL}$ | long wait time in the triple-wait-time method, s |
| $T_{WS1}$ | shortest wait time in the triple-wait-time method, s |
| $T_{WS2}$ | second shortest wait time in the triple-wait-time method, s |
| φ | porosity |
| Subscripts | |
| bvi | capillary-bound water |
| cbw | clay-bound water |
| g | gas |
| h | hydrocarbon |
| mp | most probable |
| o | oil |
| p1 | fluid phase one |
| p2 | fluid phase two |
| pw | producible water |
| t | total |
| ta | total apparent |
| w | water |

While the invention has been described with reference to a preferred embodiment, it will be appreciated by those of ordinary skill in the art that modifications can be made to the structure and form of the invention without departing from its spirit and scope which is defined in the following claims.

What is claimed is:

1. A method for conducting NMR logging measurements, comprising:
   a. providing a data acquisition sequence comprising at least two sets of CPMG pulses having relatively short recovery times $T_{WS1}$ and $T_{WS2}$, respectively, and at least one set of CPMG pulses having relatively long recovery time $T_{WL}$;
   b. receiving NMR echo signals from a population of particles in a geologic formation in response to the provided sets of CPMG pulses;
   c. processing the received NMR echo signals to determine a first and a second apparent volumes for at least one hydrocarbon fluid phase of the geologic formation, the step of processing comprising, forming a first difference signal $E_{DIF1}$ by subtracting NMR signals having relatively short recovery time $T_{WS1}$ from NMR echo signals having relatively long recovery time $T_{WL}$ and forming a second difference signal $E_{DIF2}$ by subtracting NMR signals having relatively short recovery time $T_{WS2}$ from NMR echo signals having relatively long recovery time $T_{WL}$; and
   d. providing a data representation associated with the longitudinal relaxation time constant $T_1$ of said at least one hydrocarbon fluid phase based on the determined first and second apparent volumes.

2. The method of claim 1 further comprising the step of computing $T_2$ distribution of the first difference signal $E_{DIF1}$.

3. The method of claim 2 further comprising determining a value for the $T_2$ relaxation time of said at least one hydrocarbon phase.

4. The method of claim 3 wherein the value for the $T_2$ relaxation time is determined as the most probable value based on the $T_2$ distribution of the first difference signal $E_{DIF1}$.

5. The method of claim 1 wherein the step of determining a first and second apparent volumes for said at least one hydrocarbon phase are based on the determined value for the $T_2$ relaxation time and the first and second difference signals $E_{DIF1}$ and $E_{DIF2}$.

6. The method of claim 5 wherein the step of determining said first and second apparent volumes is performed using matched filters to fit a model of the signal to each difference signal $E_{DIF1}$ and $E_{DIF2}$.

7. The method of claim 5 wherein the step of determining a first and second apparent volumes for said at least one hydrocarbon phase trains is performed by fitting the equation:

$$A(t) = A_0 e^{-\frac{t}{T_{2mp}}},$$

where $A(t)$ represents the average echo difference amplitude $E_{DIF1}$ and $E_{DIF2}$ at echo time t and $T_{2mp}$ is the most probable amplitude $T_2$ value for the hydrocarbon phase.

8. The method of claim 5 wherein the step of providing a data representation associated with the longitudinal relaxation time constant $T_1$ comprises: for each of said at least one hydrocarbon fluid phase solving the following equation for the corresponding $T_{1,pi}$ parameter:

$$\frac{e^{-\frac{T_{WS1}}{T_{1,pi}}} - e^{-\frac{T_{WL}}{T_{1,pi}}}}{e^{-\frac{T_{WS2}}{T_{1,pi}}} - e^{-\frac{T_{WL}}{T_{1,pi}}}} = \frac{A(T_{WS1}, T_{WL}, T_{1,pi})}{A(T_{WS2}, T_{WL}, T_{1,pi})}$$

where $A(T_{WS1}, T_{WL}, T_{1,pi})$ represents the apparent hydrocarbon amplitude of the $i^{th}$ hydrocarbon phase from $E_{DIF1}$, and $A(T_{WS2}, T_{WL}, T_{1,pi})$ is the apparent hydrocarbon amplitude of the $i^{th}$ hydrocarbon phase from $E_{DIF2}$.

9. The method of claim 8 further comprising the step of computing corrected hydrocarbon volumes based on the computed value for the corresponding $T_1$ parameter of said at least one hydrocarbon fluid phase.

10. The method of claim 9, wherein the corrected volumes are computed using the equation:

$$\phi_i = A_{0,E_{DIFI}} \Big/ HI_i \left( e^{-\frac{T_{WSI}}{T_{1,pi}}} - e^{-\frac{T_{WL}}{T_{1,pi}}} \right),$$

where $HI_i$ is the hydrogen index for the $i^{th}$ hydrocarbon phase.

11. The method of claim 1 further comprising the step of computing the total apparent porosity $\phi_{ta}$ of the geologic formation.

12. The method of claim 11 further comprising the step of determining the total porosity of the formation $\phi_t$ from the total apparent porosity $\phi_{ta}$ and apparent volume corrections computed based on the provided data representation associated with the longitudinal time constant(s) $T_1$ of the fluid phases.

13. The method of claim 12 further comprising the step of determining the total water volume as the difference between the total porosity and porosity associated with hydrocarbon phases.

14. The method of claim 1, wherein the first and second relatively short recovery times $T_{WS1}$ and $T_{WS2}$ are selected long enough to substantially polarize a water phase component in the population of particles.

15. The method of claim 1 wherein the recovery times $T_{WS1}$, $T_{WS2}$ and $T_{WL1}$ of the sets of CPMG pulses are selected such that water-phase contribution is substantially canceled in a difference signal formed by subtracting NMR signals corresponding to a relatively short recovery time from NMR signals corresponding to the relatively long recovery time $T_{WL1}$.

16. The method of claim 1 wherein the sets of CPMG pulses in step (a) are applied in three different frequency bands.

17. A computer software product for implementing the steps of the method of claim 1 on a computer controlling the operation of a NMR logging tool.

* * * * *